(12) United States Patent
Leonard et al.

(10) Patent No.: US 7,332,645 B2
(45) Date of Patent: Feb. 19, 2008

(54) IL-21 AS A REGULATOR OF IMMUNOGLOBIN PRODUCTION

(75) Inventors: Warren J. Leonard, Bethesda, MD (US); Katsutoshi Ozaki, Tochigi (JP); Rosanne Spolski, Ellicott City, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 11/027,868

(22) Filed: Dec. 30, 2004

(65) Prior Publication Data

US 2005/0193434 A1    Sep. 1, 2005

Related U.S. Application Data

(63) Continuation-in-part of application No. PCT/US03/20370, filed on Jun. 26, 2003.

(60) Provisional application No. 60/393,215, filed on Jul. 1, 2002.

(51) Int. Cl.
| | |
|---|---|
| *A01K 67/00* | (2006.01) |
| *A01K 67/033* | (2006.01) |
| *A01K 67/027* | (2006.01) |
| *C07H 21/02* | (2006.01) |
| *C07H 21/04* | (2006.01) |
| *C12N 15/00* | (2006.01) |

(52) U.S. Cl. ............................. 800/11; 800/9; 800/13; 800/18; 536/23.1; 435/455

(58) Field of Classification Search ............... 800/9, 800/11, 13, 18; 536/23.1; 435/455
See application file for complete search history.

(56) References Cited

U.S. PATENT DOCUMENTS 6,200,805 B1    3/2001    de Vries et al.

(Continued)

FOREIGN PATENT DOCUMENTS

WO      WO 99/61617      12/1999

(Continued)

OTHER PUBLICATIONS

Doetschmann, 1999, Lab. Animal Sci., 49: 137-143.*

(Continued)

*Primary Examiner*—Anne M. Wehbe'
*Assistant Examiner*—Joanne Hama
(74) *Attorney, Agent, or Firm*—Leydig, Voit & Mayer

(57) ABSTRACT

A transgenic mouse is disclosed herein whose somatic and germ cells comprise a disrupted IL-21 receptor gene, the disruption being sufficient to inhibit the binding of IL-21 to an IL-21 receptor, and a disrupted IL-4 gene, the disruption being sufficient to inhibit the production of IL-4 or the binding of IL-4 to the IL-4 receptor. A mouse homozygous for the disrupted IL-21 receptor gene and homozygous for the disrupted IL-4 gene has diminished B cell function. A method is disclosed for altering a B cell activity. The method includes administering a therapeutically effective amount of an agent that interferes with the interaction of IL-21 with an IL-21 receptor, thereby altering the B cell activity. A method is also disclosed for of treating a subject with Job's disorder or atopic disease. A method is also disclosed for treating or preventing an allergic reaction in a subject. A method is also disclosed for treating a subject with an autoimmune or antibody mediated disorder.

5 Claims, 7 Drawing Sheets

U.S. PATENT DOCUMENTS

| | | | |
|---|---|---|---|
| 6,307,024 | B1 | 10/2001 | Novak et al. |
| 6,313,272 | B1 | 11/2001 | Greve et al. |
| 6,358,509 | B1 | 3/2002 | Ramanthan et al. |
| 2001/0023070 | A1 | 9/2001 | Ebner et al. |
| 2002/0128446 | A1 | 9/2002 | Novak et al. |
| 2003/0003545 | A1 | 1/2003 | Ebner et al. |
| 2003/0108549 | A1 | 6/2003 | Carter et al. |
| 2003/0125524 | A1 | 7/2003 | Novak et al. |

FOREIGN PATENT DOCUMENTS

| | | |
|---|---|---|
| WO | WO 99/61617 A1 | 12/1999 |
| WO | WO 00/17235 A2 | 3/2000 |
| WO | WO 01/77171 | 10/2001 |
| WO | WO 01/77171 A2 | 10/2001 |
| WO | WO 02/10393 A2 | 2/2002 |
| WO | WO 03/040313 | 5/2003 |
| WO | WO 03/040313 A2 | 5/2003 |
| WO | WO 03/082212 | 10/2003 |
| WO | WO 03/082212 A2 | 10/2003 |

OTHER PUBLICATIONS

Moens et al., 1993, Development, 119: 485-499.*
Jacks et al., 1992, Nature, 359: 295-300.*
Kuehn et al., 1987, Nature, 326, 295-298.*
Jaenisch, 1988, Science, 240, 1468-1474.*
Racay, 2002, Bratisl Lek Listy, 103: 121-126.*
Gerlai, 1996, Trends Neurosci, 19: 177-181.*
Minchin et al., 2001, J. of Pharm. and Exp. Therap., 296: 1006-1012.*
Asao, et al., "Cutting Edge: The Common γ-Chain is an Indispensable Subunit of the IL-21 Receptor Complex," *J. Immunol.*, 167:1-5 (2001).
Brenne, et al., "Interleukin-21 is a growth and survival factor for human myeloma cells," *Blood*, 99(10):3756-3762 (May 15, 2002).
Driver, et al., "Development and Maintenance of a B220⁻ Memory B Cell Compartment," *Immunol.*, 167:1393-1405 (2001).
Kasaian, et al., "Il-21 limits NK cell responses and promotes antigen-specific T cell activation: a mediator of the transition from innate to adaptive immunity," *Immunity*, 16(4):559-569 (2002).
Kovanen and Leonard, "Cytokines and immunodeficiency diseases: critical roles of the $\gamma_c$-dependent cytokines interleukins 2, 4, 7, 9, 15, and 21, and their signaling pathways," *Immunol. Reviews*, 202:67-83 (2004).
Leonard, "Cytokines and Immunodeficiency Diseases," *Nature Rev. Immunol.*, 1:200-208 (Dec. 2001).
McHeyzer-Williams, et al., "Antigen-specific B Cell Memory: Expression and Replenishment of a Novel B220-Memory B Cell Compartment," *J. Exp. Med.*, 191(7):1149-1165 (2000).
Mehta, et al., "Biology of IL-21 and the IL-21 receptor," *Immunol. Reviews*, 202-84-95 (2004).
Ozaki, et al., "Cloning of a type I cytokine receptor most related to the IL-2 receptor β chain," *Proc. Natl. Acad. Sci. USA* 97(21):11439-11444 (2000).
Ozaki, et al., "A Critical Role for IL-21 in Regulating Immunoglobulin Production," *Science*, 298:1630-1634 (Nov. 22, 2002).
Ozaki, et al., "Regulation of B cell differentiation and plasma cell generation by IL-21, a novel inducer of Blimp-1 and Bcl-6," *J Immunology*, 173(9):5361-5371 (Nov. 1, 2004).
Parrish-Novak, et al., "Interleukin 21 and its receptor are involved in NK cell expansion and regulation of lymphocyte function," *Nature*, 408:57-63 (Nov. 2, 2000).
Suto, et al., "Interleukin 21 prevents antigen-induced IgE production by inhibiting germ line Cε transcription of IL-4-stimulated B cells," *Blood*, 100(13):4565-4573 (Dec. 15, 2002).
Suzuki, et al., "Janus kinase 3 (Jak3) is essential for common cytokine receptor γ chain ($\gamma_c$)-dependent signaling: comparative analysis of $\gamma_c$, Jak3, and $\gamma_c$ and Jak3 double-deficient mice," *International Immunol.*12(2):123-132 (2000).
Ukai, et al., "Formation of an Active Form of the Interleukin-21 15 Receptor β-Chain by Insertion of the Intracisternal A Partical in a Radiation-Induced Mouse Thymic Lymphoma and its Role in Tumorigenesis," *MolecularCarcinogenesis*, 37:110-119 (2003).
Voβhenrich and Di Santo, "Cytokines: IL-21 joines teh $\gamma_c$-dependent network?" *Current Biology*, 11:R175-R177 (2001).
Asao et al., *J. Immunol.*, 167, 1-5 (2001).
Brenne et al., *Blood*, 99(10), 3756-3762 (2002).
Driver et al., *Journal of Immunol.*, 167, 1393-1405 (2001).
GenBank Accession No. AF254069 (2001).
GenBank Accession No. AF254070 (2000).
GenBank Accession No. NM_000206 (2006).
GenBank Accession No. NM_013563 (2006).
GenBank Accession No. NM_021782 (2005).
GenBank Accession No. NM_021798 (2006).
GenBank Accession No. NM_021803 (2000).
GenBank Accession No. NM_021887 (2005).
GenBank Accession No. NM_181078 (2006).
GenBank Accession No. NM_181079 (2006).
Habib et al., *Biochemistry*, 41(27), 8725-8731 (2002).
Kasaian et al., *Immunity.*, 16(4), 559-569 (2002).
Kovanen et al., *Immunol. Reviews*, 202, 67-83 (2004).
Leonard, *Nature Rev. Immunol.*, 1, 200-208 (2001).
Mcheyzer-Williams et al., *J. Exp. Med.*, 191(7), 1149-1165 (2000).
Mehta et al., *Immunol. Reviews*, 202, 84-95 (2004).
Noben-Trauth et al., *Proc. Natl. Acad. Sci.*, 94, 10838-10843 (1997).
O'Shea et al., *Cell*, 109, S121-S131 (2002).
Ozaki et al., *J. Immunology*, 173 (9), 5361-5371 (2004).
Ozaki et al., *Proc. Natl. Acad. Sci. USA*, 97(21), 11439-11444 (2000).
Ozaki et al., *Science*, 298, 1630-1634 (2002).
Parrish-Novak et al., *Nature*, 408, 57-63 (2000).
Sugamura et al., *Ann. Rev. Immunol.*, 14, 179-205 (1996).
Suto et al., *Blood*, 100(13), 4565-4573 (2002).
Suzuki et al., *International Immunol.*, 12(2), 123-132 (2000).
Ukai et al., *Molecular Carcinogenesis*, 37, 110-119 (2003).
Voβhenrich et al., *Current Biology*, 11, R175-R177 (2001).

* cited by examiner

A

B

C

D

E

F

IL-21 AS A REGULATOR OF IMMUNOGLOBIN PRODUCTION

RELATED APPLICATIONS

This is a Continuation-in-Part (CIP) of PCT Application No. PCT/US2003/020370, filed Jun. 26, 2003, which claims benefit of U.S. Provisional Application No. 60/393,215, filed Jul. 1, 2002. The disclosures of PCT Application No. PCT/US2003/020370 and Provisional Application No. 60/393,215 are incorporated herein by reference.

FIELD

This application relates to the field of immunology, specifically to the use of agents that inhibit the interaction of IL-21 with the IL-21 receptor to modulate an immune response, such as a B cell activity.

BACKGROUND

Cytokines exert their respective biochemical and physiological effects by binding to specific receptor molecules. Receptor binding then stimulates specific signal transduction pathways (Kishimoto et al., *Cell* 76:253-262, 1994). The specific interactions of cytokines with their receptors can be the primary regulators of a wide variety of cellular processes including activation, proliferation, and differentiation of cells (Arai et al., *Ann. Rev. Biochem.* 59:783-836, 1990; Paul and Seder, *Cell* 76:241-251, 1994).

IL-21 was isolated from a cDNA library derived from activated CD3 (+) T-cells (Parrish-Novak et al., *Nature* 408 57-63, 2000). The IL-21 cDNA encodes a secreted protein of 131 amino acids protein most closely related to IL-2 and IL-15. The IL-21 gene has been mapped to human chromosome 4q26-q27 near the IL-2 gene.

IL-21 mRNA is expressed in activated CD4+ but not in activated CD8+ T-cells. In addition, IL-21 was expression was not detected in B-cells and monocytes (Parrish-Novak et al., *Nature* 408:57-63, 2000). However, it has been demonstrated that IL-21 stimulates proliferation of B-cells that are stimulated by cross-linking of the CD40 antigen and proliferation stimulated by IL-4 in addition to anti-IgM. IL-21 has also been shown to stimulate proliferation of naive (CD45RA+) cells, but not memory (CD45RO+) T-cells, mediated by engagement of CD3. IL-21 has also been shown to stimulate the proliferation of bone marrow progenitor to cells and to enhance the expression of the NK-cell marker CD56 in the presence of IL-15 (for review, see Horst Ibelgaufts' COPE: Cytokines Online Pathfinder Encyclopaedia, available on the internet).

The IL-21 receptor has been isolated and was found to be expressed by CD23+ B-cells, B-cell lines, a T-cell leukemia line, and NK-cell lines. The receptor gene has been mapped to human chromosome 16p12 (see Parrish-Novak et al., *Nature* 408:57-63, 2000; Ozaki et al., *Proc. Natl. Acad. Sci. USA* 97:11439-11444, 2000).

The IL-21 receptor (IL-21R) is 538 amino acids, and is most closely related to human IL-2 receptor beta chain. The IL-21R forms heterodimers with the common cytokine receptor gamma chain, which is an indispensable subunit of the functional receptor complexes for IL-2, IL-4, IL-7, IL-9, and IL-15, and has been shown also to be part of the IL-21 receptor complex. The functional signaling complex activates has been demonstrated to activate the Janus kinase (Jak1, Jak3) and the Stat proteins (see Asao et al., *J. Immunol.* 167:1-5, 2000). However, the effects of IL-21 on B cell activity have not yet been fully elucidated.

SUMMARY

Method are disclosed herein for altering a B cell activity. The methods include administering a therapeutically effective amount of an agent that interferes with the interaction of IL-21 with an IL-21 receptor, thereby altering the B cell activity.

A transgenic mouse is disclosed herein whose somatic and germ cells comprise a disrupted IL-21 receptor gene, the disruption being sufficient to inhibit the binding of IL-21 to the IL-21 receptor, and a disrupted IL-4 gene, the disruption being sufficient to inhibit the production of IL-4 or the binding of IL-4 to the IL-4 receptor, the disrupted IL-21 receptor and IL-4 genes being introduced into the mouse or an ancestor of the mouse at an embryonic stage. A mouse homozygous for the disrupted IL-21 receptor gene and homozygous for the disrupted IL-4 gene has diminished B cell function.

In one embodiment, a transgenic mouse is disclosed whose genome is heterozygous for an engineered disruption in an IL-21 receptor gene and whose genome is heterozygous for an engineered disruption in an IL-4 gene. The engineered IL-21 receptor gene and the engineered IL-4 gene in a homozygous state inhibits production of a functional IL-21 receptor and a functional IL-4, and the transgenic mouse is deficient for production of an immunoglobulin.

In yet another embodiment, a method is disclosed for treating a subject with Job's disorder. The method includes administering to the subject a therapeutically effective amount of IL-21 or an agonist thereof, thereby ameliorating a sign or a symptom of Job's disorder.

In a further embodiment, a method is also disclosed for treating or preventing an allergic reaction in a subject. The method includes administering to the subject a therapeutically effective amount of an agent that inhibits the interaction of IL-21 with its receptor, thereby treating or preventing the allergic reaction.

The disclosure also provides methods for treating an autoimmune disorder, such as systemic lupus erythematosus ("SLE") in a subject by administering a a prophylactically or therapeutically effective amount of an antagonist that inhibits binding of IL-21 with its receptor, or that inhibits IL-21 induced signaling.

The foregoing and other features and advantages will become more apparent from the following detailed description of several embodiments, which proceeds with reference to the accompanying figures.

BRIEF DESCRIPTION OF THE FIGURES

FIGS. 1B and 1C are digital images of genomic Southern blot analysis of tail DNA from wild type (+/+), heterozygous (+/−), and IL-21R knockout (−/−) mice. Genomic DNA (5-10 μg) from littermates were digested with Bgl II or EcoRI and Xho I, separated on agarose gel, transferred to nylon membranes, and hybridized with 5' (FIG. 1B) or 3' (FIG. 1C) flanking probes. The expected band sizes are shown. FIG. 1D is a digital image of RT-PCR of IL-21R or G3PDH as a control gene from wild type and IL-21R$^{-/-}$ mice. Total RNA was prepared from thymus or Th2-differentiated cells of each littermate. 1 μg of total RNA was used for reverse transcription and 10% of the product was used to PCR amplify IL-21R (upper panel) or G3PDH (lower panel). The 5' and 3' IL-21R primers were 5'-ATGCCCCGGGGCCCAGTGGCTG-3' (SEQ ID NO: 1) and 5'-CACAGCATAGGGGTCTCTGAGGTTC-3' (SEQ ID NO:2); 5' and 3' primers for G3PDH were 5'-ATGGTGAAGGTCGGTGTGAACGG-3' (SEQ ID NO:3) and 5'-CCCTTCCACAATGCCAAAGTTGTC-3' (SEQ ID NO:4). FIGS. 1E and 1F are digital images of a Northern blot analysis of IL-4Rα expression using 25 μg of total RNA from day 7 Th2-differentiated cells stimulated overnight with IL-4 (FIG. 1E) or RNA from unstimulated thymocytes (FIG. 1F). In FIGS. 1E and 1F, the upper panel shows expression of IL-4Rα and the lower panel shows expression of pHe7 control. The IL-4Rα cDNA probe was prepared by RT-PCR from Th2-differentiated cells with primers, 5'-ATGGGGCGGCTTTGCACCAAG-3' (SEQ ID NO:5) and 5'-TAGGACTCCACTCACTCCAGG-3' (SEQ ID NO:6). Mice derived from two distinct IL-21R$^{+/-}$ ES cells that were generated in different transgenic core facilities were analyzed.

FIG. 2A is a bar graph of normal Th1 and Th2 polarization of IL-21R$^{-/-}$ lymphocytes. Splenic CD4$^+$ T cells were positively-selected using a varioMACS (Milteny) and stimulated with plate-coated anti-CD3 (2 μg/ml) and soluble anti-CD28 (2 μg/ml) for 3 days under Th1 (IL-12 and 10 μg/ml anti-IL4) or Th2 (IL-4 and 10 μg/ml anti-IFNγ) polarizing conditions; after extensive washing, cells were incubated overnight with plate-coated anti-CD3 (2 μg/ml). FIGS. 2B and 2C are bar graphs of data obtained nine days after a single subcutaneous injection of 400 μg KLH in CFA. Draining lymph nodes were isolated from mice and single cell suspensions were cultured at 5×10$^5$ cells/well in 96-well plates with the indicated concentration of KLH. The supernatant was harvested after 96 hours and IFNγ and IL-4 (FIGS. 2B and 2C) concentration were determined by ELISA (BD Pharmingen) or (FIG. 2D) cells were pulsed with 1 μCi [$^3$H]-thymidine for the last 16 hours of culture. (FIGS. 2E and F) IFNγ and IL-4 production as in (B) and (C), but cells were stimulated with anti-CD3. Shown are mean±S.E.M. from three IL-21R$^{-/-}$ and three wild type mice (FIG. 2A) or five IL-21R$^{-/-}$ and five wild type mice (FIG. 2B-F).

In FIGS. 3A and 3B, 100 μg ovalbumin (Pierce) in 100 μl PBS was mixed with 100 μl complete Freunds Adjuvant (CFA) (Pierce) and injected intraperitoneally. Two weeks later, mice were similarly injected with 100 μg ovalbumin in IFA (Pierce), and after an additional week, serum Ig levels were assessed by ELISA. The capture antibody, control Ig, secondary HRP-conjugated anti-mouse antibodies for each Ig subclass, ELISA kit for mouse IgE, and HRP substrate were from BD PharMingen or Southern Biotechnology Associates, Inc. For antigen-specific ELISAs, the secondary antibody and substrate were the same as above, but the antigen was coated overnight at 5 μg/ml in PBS. The data are from a total of 8 mice in each group, and three independent experiments. For FIGS. 3C and D, 400 μg of KLH in 200 μl PBS was mixed with 200 μl CFA and the emulsion was injected into footpads, bottom of tail, and back, similar to a published protocol (Chen et al., Nature 407: 916, 2000; Dong et al., Nature 409:97,2001). At day 9, serum Ig levels were determined. The data are from a total of six mice in each group and three independent experiments. In FIGS. 3A and 3C, shown are the mean±S.E.M. FIGS. 3B and 3D are representative results from three experiments.

In FIGS. 5A and 5B, cells were isolated using B220 (CD45R) magnetic beads from naïve mice and stimulated with IL-4 plus either anti-CD40 or LPS. Production (mean±S.E.M.) of IgG1 at day 4 (FIG. 5A) and IgE at day 7 (FIG. 5B) were measured by ELISA. (C) 4-hydroxy-3-nitrophenyl acetyl-conjugated KLH (NP-KLH) 400 μg in 100 μl PBS was mixed with 100 μl Ribi adjuvant (purchased from Corixa Corporation, MT) and injected intraperitoneally. Twelve days later, serum Ig and antibody-forming cells (AFCs) number were measured by ELISA and ELISPOT. For ELISPOT assays, plates (Multi-Screen, Millipore) were pre-coated with 50 μg/ml 4-hydroxy-3-iodo-5-nitrophenyl acetyl-conjugated BSA (NIP-BSA). The secondary Ab was as described for the ELISA assays. AEC (Sigma-Aldrich) was the HRP substrate. Positive colonies were counted by microscope. NP-KLH, NIP-BSA, and activated NP were from Biosearch Technologies Inc, CA. APC was from Prozyme (CA). For the results shown in FIG. 5C, splenocytes were stained with NP-APC, IgD-FITC, B220-PE or Syndecan-PE, CD4-PECy5, CD8-PECy5, F4/80-PECy5, and propidium iodide. NP-specific antibody expressing cells that were, negative for staining with IgD, CD4, CD8, F4/80, and propidium iodide are indicated as box. FIG. 5D shows the number of NP-specific IgG1, IgM, and IgE forming cells in splenocytes determined by ELISPOT. Shown are mean±S.E.M. from four IL-21R$^{-/-}$ and three wild type mice. Levels of IgE forming cell were below the limits of detection.

FIG. 6B are FACS plots of CD23 vs. CD21 and CD21 vs. IgM profiles from IL-4$^{-/-}$IL-21R$^{-/-}$ and wild type mice splenic B cells. FIG. 6C are bar graphs of the total serum IgG and IgM from naïve IL-2 R$^{-/-}$ and wild type mice that were measured by ELISA. Shown are mean±S.E.M. from four IL-4$^{-/-}$IL-21R$^{-/-}$ and four wild type mice.

SEQUENCE LISTING

Figure 1:
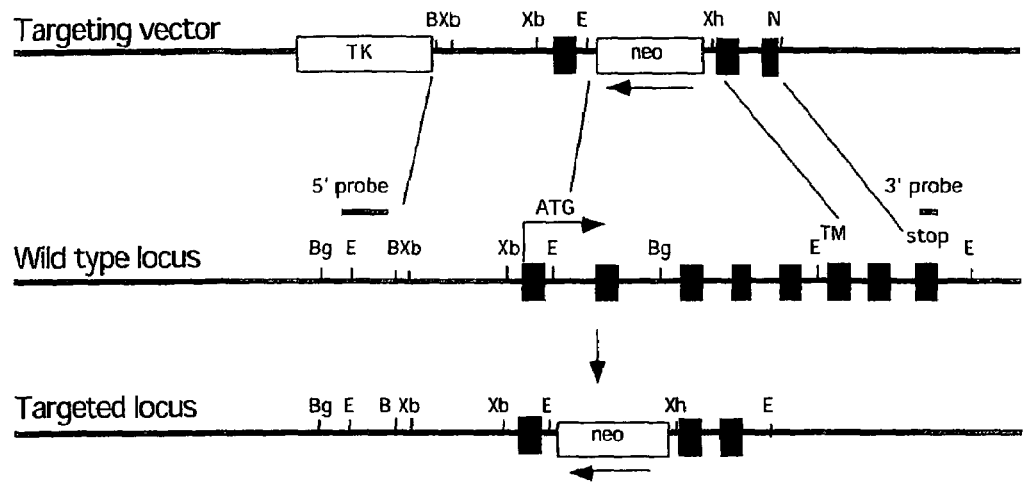
FIG. 1 is a set of images demonstrating the generation of IL-21R$^{-/-}$ mice. A BAC clone library prepared from 129sv mice (Genome Systems) was screened using a probe used to identify murine IL-21R cDNAs (1). A clone that by restriction enzyme mapping contained all IL-21R coding exons was identified, and a targeting construct was designed to delete the coding region (see the diagram shown in FIG. 1A), extending from the signal peptide to the transmembrane domain, so that only 5 amino acids of the signal peptide were retained; the residual part of the cytoplasmic domain was frame-shifted. The targeting construct has 4 kb (BamHI/EcoRI) and 2 kb (XhoI/NheI) 5' and 3' flanking fragments, respectively. Shown is the targeting construct, wild type genomic locus and the homologously recombined locus. 5' and 3' flanking probes are indicated. B, BamHI; E, Eco RI; Xb, Xba I; Xh, Xho I. ATG and Stop indicate the start and stop codons; TM indicates the transmembrane region.
Figure 1:
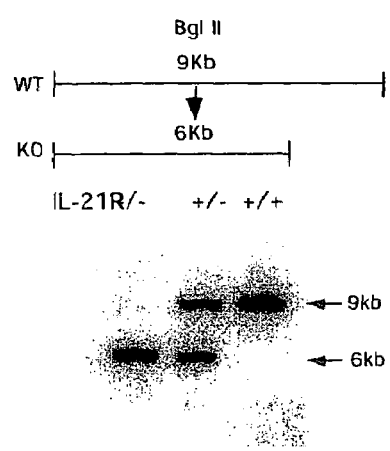
Figure 1:
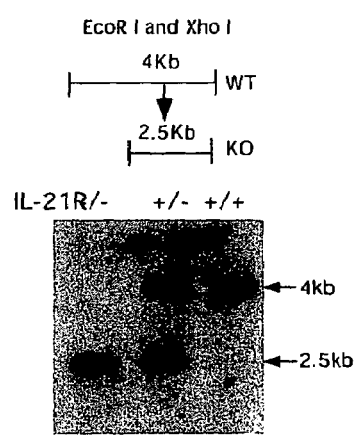
Figure 1:
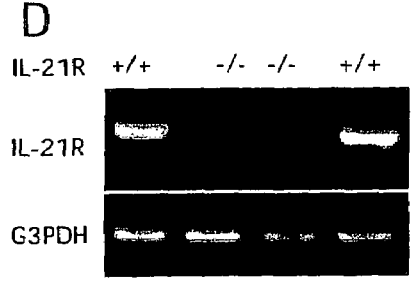
Figure 1:
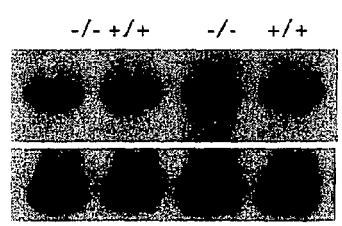
Figure 1:
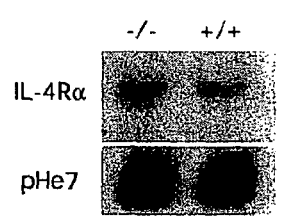

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NOs: 1-6 are primer nucleic acid sequences.

DETAILED DESCRIPTION

Terms

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

Animal: Living multicellular vertebrate organisms, a category that includes, for example, mammals, primates, and birds.

Agonist: An agent that has affinity for and stimulates physiologic activity at cell receptors normally stimulated by naturally occurring substances, thus triggering a biochemical response. An IL-21 and/or IL-21 receptor agonist has affinity for the IL-21 receptor and stimulates an activity induced by the binding of IL-21 with its receptor. For example, an IL-21/IL-21 receptor agonist is a molecule that binds to the IL-21 receptor and induces intracellular signaling via the Jak/Stat signaling pathway. In contrast, an "antagonist" is an agent that inhibits activity of a cell receptor normally stimulated by a naturally occurring substance. Accordingly, an IL-21/IL-21 receptor antagonist binds to IL-21 or to the IL-21 receptor and inhibits binding of IL-21 to the IL-21 receptor and/or inhibits an activity normally induced by binding of IL-21 with its receptor. For example, an IL-21/IL-21 receptor antagonist can bind to IL-21 or to the IL-21 receptor and diminish or prevent binding, for example, by blocking binding, of IL-21 to the IL-21 receptor. Alternatively, and IL-21/IL-21 receptor antagonist can bind to the IL-21 receptor and diminish or prevent downstream signaling that would normally be induced by the binding of IL-21 with its receptor, such as activation of the Jak/Stat intracellular signaling pathway. Agonists and antagonists can include a variety of classes of molecules including polypeptides, such as ligand-like polypeptides, antibodies, and fragments or subsequences thereof. Agonists and antagonists can also include fusion polypeptides, antibodies, peptides (such as peptides of less than about 20 amino acids in length), and small molecules. Exemplary antagonists include: neutralizing antibodies specific for IL-21 and the IL-21 receptor, soluble IL-21 receptor molecules, and IL-21 receptor fusion proteins, such as IL-21R-immunoglobulin Fc molecules. Exemplary antagonists can be found, e.g., in U.S. patent application nos. 2002/0128446, 2003/0125524 and 2003/0108549.

Antibiotic Resistance Cassette: A nucleic acid sequence encoding a selectable marker that confers resistance to that antibiotic in a host cell in which the nucleic acid is translated. Examples of antibiotic resistance cassettes include, but are not limited to: kanamycin, ampicillin, tetracycline, chloramphenicol, neomycin, hygromycin, and zeocin.

Antibody: Immunoglobulin molecules and immunologically active portions of immunoglobulin molecules, i.e., molecules that contain an antigen binding site which specifically binds (immunoreacts with) an antigen. In one embodiment the antigen is the IL-4 or IL-21. In another embodiment, the antigen is the IL-4 or the IL-21 receptor.

A naturally occurring antibody (e.g., IgG) includes four polypeptide chains, two heavy (H) chains and two light (L) chains inter-connected by disulfide bonds. However, the antigen-binding function of an antibody can be performed by fragments of a naturally occurring antibody. Thus, these antigen-binding fragments are also intended to be designated by the term antibody. Examples of binding fragments encompassed within the term antibody include (i) an Fab fragment consisting of the VL, VH, CL and CH1 domains; (ii) an Fd fragment consisting of the VH and CH1 domains; (iii) an Fv fragment consisting of the VL and VH domains of a single arm of an antibody, (iv) a dAb fragment (Ward et al., *Nature* 341:544-6, 1989) which consists of a VH domain; (v) an isolated complimentarily determining region (CDR); and (vi) an F(ab')$_2$ fragment, a bivalent fragment comprising two Fab fragments linked by a disulfide bridge at the hinge region. Furthermore, although the two domains of the Fv fragment are coded for by separate genes, a synthetic linker can be made that enables them to be made as a single protein chain (known as single chain Fv (scFv); Bird et al. *Science* 242:423-6, 1988; and Huston et al., *Proc. Natl. Acad. Sci. USA* 85:5879-83, 1988) by recombinant methods. Such single chain antibodies are also included.

In one embodiment, antibody fragments for use in inhibiting the action of IL-4 or IL-21 are those which are capable of crosslinking their target antigen, e.g., bivalent fragments such as F(ab')$_2$ fragments. Alternatively, an antibody fragment which does not itself crosslink its target antigen (e.g., a Fab fragment) can be used in conjunction with a secondary antibody which serves to crosslink the antibody fragment, thereby crosslinking the target antigen. Antibodies can be fragmented using conventional techniques and the fragments screened for utility in the same manner as described for whole antibodies. An antibody is further intended to include bispecific and chimeric molecules that specifically bind the target antigen.

"Specifically binds" refers to the ability of individual antibodies to specifically immunoreact with an antigen, such as IL-4, IL-21, the IL-4 receptor, or the IL-21 receptor. The binding is a non-random binding reaction between an antibody molecule and an antigenic determinant of the target cytokine or receptor. The desired binding specificity is typically determined from the reference point of the ability of the antibody to differentially bind the target cytokine or receptor and an unrelated antigen, and therefore distinguish between two different antigens, particularly where the two antigens have unique epitopes. An antibody that specifically binds to a particular epitope is referred to as a "specific antibody".

Antisense, Sense, and Antigene: Double-stranded DNA (dsDNA) has two strands, a 5'->3' strand (plus strand) and a 3'->5' strand (minus strand). Because RNA polymerase adds nucleic acids in a 5'->3' direction, the minus strand of the DNA serves as the template for the RNA during transcription. Thus, the RNA formed will have a sequence complementary to the minus strand, and identical to the plus strand (except that the base uracil is substituted for thymine).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a DNA target.

B Cell: A subset of lymphocytes, that is, white blood cells (leukocytes). Mature B cells differentiate into plasma cells, which produces antibodies, and memory B cells. A "B cell progenitor" is a cell that can develop into a mature B cell. B cell progenitors include stem cells, early pro-B cells, late pro-B cells, large pre-B cells, small pre-B cells, and immature B cells. Generally, early pro-B cells (that express, for example, CD43 or B220) undergo immunoglobulin heavy chain rearrangement to become late pro B and pre B cells, and further undergo immunoglobulin light chain rearrangement to become an immature B cells. Immature B cells include T1 and T2 B cells. Thus, one example of an immature B cell is a T1 B that is an AA41$^{hi}$CD23$^{lo}$ cell. Another example of an immature B cell is a T2 B that is an AA41$^{hi}$CD$_{23}$$^{hi}$ cell. Thus, immature B cells include B220 (CD45R) expressing cells wherein the light and the heavy chain immunoglobulin genes are rearranged, and that express AA41. In one embodiment, immature B cells express CD45R, class II, IgM, CD19 and CD40. Immature B cells do not exhibit surrogate light chain expression, but do express Ig αβ and RAG. Immature B cells can develop into mature B cells, which can produce immunoglobulins (e.g., IgA, IgG or IgM). Mature B cells have acquired surface IgM and IgD, are capable of responding to antigen, and express characteristic markers such as CD21 and CD23 (CD23$^{hi}$CD21$^{hi}$ cells), but do not express AA41. B cells can be activated by agents such as lippopolysaccharide (LPS) or IL-4 and antibodies to IgM. Common biological sources of B cells and B cell progenitors include bone marrow, peripheral blood, spleen and lymph nodes. Plasma cells are terminally differentiated B cells that are the predominant antibody-secreting cells. Memory B cells are small, long-lived B lymphocytes produced following antigen stimulation. Typically, memory B cells express high affinity antigen specific immunoglobulin (B cell receptor) on their cell surface.

Comprises: A term that means "including." For example, "comprising A or B" means including A or B, or both A and B, unless clearly indicated otherwise.

Cytokine/Interleukin (IL): A generic name for a diverse group of soluble proteins and peptides which act as humoral regulators at nano- to picomolar concentrations and which, either under normal or pathological conditions, modulate the functional activities of individual cells and tissues. These proteins also mediate interactions between cells directly and regulate processes taking place in the extracellular environment. Many growth factors and cytokines act as cellular survival factors by preventing programmed cell death. Cytokines and interleukins include both naturally occurring peptides and variants that retain full or partial biological activity. Although several cytokines/interleukins are described in the specification, they are not limited to the specifically disclosed peptides.

Deletion: The removal of a sequence of nucleic acid, such as DNA.

DNA (deoxyribonucleic acid): DNA is a long chain polymer which comprises the genetic material of most living organisms (some viruses have genes comprising ribonucleic acid, RNA). The repeating units in DNA polymers are four different nucleotides, each of which comprises one of the four bases, adenine, guanine, cytosine, and thymine bound to a deoxyribose sugar to which a phosphate group is attached. Triplets of nucleotides, referred to as codons, in DNA molecules code for amino acid in a polypeptide. The term codon is also used for the corresponding (and complementary) sequences of three nucleotides in the mRNA into which the DNA sequence is transcribed.

Electroporation: A method of inducing or allowing a cell to take up macromolecules by applying electric fields to reversibly permeabilize the cell walls. Various methods and apparatuses used are further defined and described in: U.S. Pat. No. 4,695,547; U.S. Pat. No. 4,764,473; U.S. Pat. No. 4,882,28; and U.S. Pat. Nos. 4,946,793; 4,906,576; 4,923, 814; and 4,849,089.

Eukaryotic cell: A cell having an organized nucleus bounded by a nuclear membrane. These include simpler organisms such as yeasts, slime molds, and the like, as well as cells from multicellular organisms such as invertebrates, vertebrates, and mammals. Multicellular organisms include a variety of cell types, such as: endothelial cell, smooth muscle cell, epithelial cell, hepatocyte, cells of neural crest origin, tumor cell, hematopoetic cell, immunologic cell, T cell, B cell, monocyte, macrophage, dendritic cell, fibroblast, keratinocyte, neuronal cell, glial cell, adipocyte, myoblast, myocyte, chondroblast, chondrocyte, osteoblast, osteocyte, osteoclast, secretory cell, endocrine cell, oocyte, and spermatocyte. These cell types are described in standard histology texts, such as McCormack, Introduction to Histology,© 1984 by J.P. Lippincott Co.; Wheater et al., eds., Functional Histology, 2nd Ed.,© 1987 by Churchill Livingstone; Fawcett et al., eds., Bloom and Fawcett: A Textbook of Histology,© 1984 by William and Wilkins.

ES (embryonic stem) cells: Cells derived from the inner cell mass or epiblast of the blastocyst that are capable of undergoing an unlimited number of symmetrical divisions without differentiating. Embryonic stem cells exhibit and maintain a stable, full complement of chromosomes and can give rise to differentiated cell types that are derived from all three primary germ layers of the embryo (endoderm, mesoderm, and ectoderm). They are capable of integrating into all fetal tissues, and mouse ES cells maintained in culture for long periods of time can still generate any tissue when they are reintroduced into an embryo to generate a chimeric animal. ES cells are also capable of colonizing the germ line and giving rise to egg or sperm cells.

ES cells are clonogenic, meaning that a single ES cell can give rise to a colony of genetically identical cells that have the same properties as the original cell. In addition, mouse ES cells express the transcription factor, Oct-4, which activates or inhibits a number of target genes and maintains the ES cells in a proliferative, non-differentiating state, though they can be induced to differentiate.

ES cells lack the G1 checkpoint in the cell cycle; they spend most of their time in the S phase of the cell cycle, during which they synthesize DNA. Unlike differentiated somatic cells, ES cells do not require any external stimulus to initiate DNA replication. In addition, ES cells do not show X inactivation.

Foreign gene: Any nucleic acid (e.g., gene sequence) that is introduced into the genome of an animal by experimental manipulations and can include gene sequences found in that animal so long as the introduced gene contains some modification (e.g., a point mutation, the presence of a selectable marker gene, a non-native regulatory sequence, or a native sequence integrated into the genome at a non-native location, etc.) relative to the naturally-occurring gene.

Gene: A DNA sequence that comprises control and coding sequences necessary for the production of a polypeptide or protein. The polypeptide can be encoded by a full-length coding sequence or by any portion of the coding sequence in some embodiments, so long as at least a portion of the desired activity of the polypeptide is retained.

Homologous recombination: An exchange of homologous polynucleotide segments anywhere along a length of two (or more) nucleic acid molecules. Homologous recombination provides a method for introducing a desired gene sequence into a plant or animal cell. Thus, it is capable of producing chimeric or transgenic plants and animals having defined, and specific, gene alterations. A discussion of the process of homologous recombination can be found in Watson, J. D., In: *Molecular Biology of the Gene*, 3rd Ed., W. A. Benjamin, Inc., Menlo Park, Calif. (1977).

In brief, homologous recombination is a well-studied natural cellular process that results in the scission of two nucleic acid molecules having identical or substantially similar sequences (i.e. "homologous"), and the ligation of the two molecules such that one region of each initially present molecule is now ligated to a region of the other initially present molecule (Sedivy, *Bio-Technol.* 6:1192-1196, 1988). Homologous recombination is, thus, a sequence-specific process by which cells can transfer a "region" of DNA from one DNA molecule to another. As used herein, a "region" of DNA is intended to generally refer to any nucleic acid molecule. The region can be of any length from a single base to a substantial fragment of a chromosome.

For homologous recombination to occur between two DNA molecules, the molecules can possess a "region of homology" with respect to one another. Such a region of homology can be at least 1.5 Kb long. Two DNA molecules possess such a "region of homology" when one contains a region whose sequence is so similar to a region in the second molecule that homologous recombination can occur. Recombination is catalyzed by enzymes that are naturally present in both prokaryotic and eukaryotic cells.

Interleukin (IL)-4: IL-4 is a protein produced mainly by a subpopulation of activated T-cells (CD4$^+$TH2 cells), which also secrete IL-5 and IL-6. IL-4 is 129 amino acids (20 kDa) that is synthesized as a precursor containing a hydrophobic secretory signal sequence of 24 amino acids. IL-4 is glycosylated at two arginine residues (positions 38 and 105) and contains six cysteine residues involved in disulfide bond formation. Some glycosylation variants of IL-4 have been described that differ in their biological activities. A comparison of murine and human IL-4 shows that both proteins only diverge at positions 91-128.

The human IL-4 gene contains four exons and has a length of approximately 10 kb. It maps to chromosome 5q23-31, while the murine gene maps to chromosome 11. At the nucleotide level the human and the murine IL-4 gene display approximately 70 percent homology.

Two forms of the IL-4 receptor are known. Both IL-4 receptors include an IL-4Rα polypeptide. A T cell form of the IL-4 receptor also includes the $\gamma_c$ (the common cytokine receptor gamma chain) polypeptide. An alternative form, which is found in cells other than T cells, including B cells, contains IL-13Rα1 instead of $\gamma_c$. Il-4 induced signaling is mediated via the Jak/Stat pathway (e.g., Jak1, Jak3, Stat6) and IRS family proteins.

The biological activities of IL-4 are species-specific; mouse IL-4 is inactive on human cells and human IL-4 is inactive on murine cells. IL-4 promotes the proliferation and differentiation of activated B-cells, the expression of class II MHC antigens, and of low affinity IgE receptors in resting B-cells. In addition, IL-4 is known to enhance expression of class II MHC antigens on B-cells. This cytokine also can promote the B-cells' capacity to respond to other B-cell stimuli and to present antigens for T-cells.

The classical detection method for IL-4 is a B-cell costimulation assay measuring the enhanced proliferation of stimulated purified B-cells. IL-4 can be detected also in bioassays, employing IL4-responsive cells (e.g. BALM-4, BCL1, CCL-185, CT.4S, amongst others). A specific detection method for human IL-4 is the induction of CD3 in a number of B-cell lines with CD23 detected either by flow-through cytometry or by a fluorescence immunoassay. An alternative and entirely different detection method is RT-PCR (for review see: Boulay and Paul, *Current Opinion in Immunology* 4:294-8, 1992; Paul and Ohara, *Annual Review of Immunology* 5:429-59, 1987).

IL-21: A cytokine cloned from a cDNA library derived from activated CD3+ T-cells (Parrish-Novak et al., *Nature* 408:57-63, 2000). The IL-21 cDNA encodes a secreted protein of 131 amino acids protein most closely related to IL-2 and IL-15. The IL-21 gene has been mapped to human chromosome 4q26-q27 near the IL-2 gene. A nucleic acid sequence and polypeptide sequence for murine IL-21 is available at the NCBI website as GENBANK® Accession No. NM021782 and GENBANK® Accession No. AF254070. A nucleic acid and polypeptide sequence of human IL-21 is available at the NCBI website as GENBANK® Accession No. NM021803 and GENBANK® Accession No. AF254069. These GENBANK® entries are incorporated by reference herein.

IL-21 mRNA has been demonstrated to be expressed in activated CD4+ cells, but not in other T cells, B-cells, or monocytes (Parrish-Novak et al., *Nature* 408:57-63, 2000). However, it has been demonstrated that IL-21 stimulates proliferation of B-cells that are stimulated by cross-linking of the CD40 antigen and proliferation of B cells stimulated by IL-4 in addition to anti-IgM. IL-21 has also been shown to stimulate proliferation of naive (CD45RA (+)) cells, mediated by engagement of CD3. IL-21 has also been shown to stimulate the proliferation of bone marrow progenitor to cells and to enhance the expression of the NK-cell marker CD56 in the presence of IL-15. (For review, see Horst Ibelgaufts' COPE: Cytokines Online Pathfinder Encyclopaedia, available on the internet).

The IL-21 receptor has been isolated and was found to be expressed by CD23+ B-cells, B-cell lines, a T-cell leukemia line, and NK-cell lines. The functional IL-21 receptor is a dimer composed of an IL-21 receptor molecule and an IL-2 receptor common gamma ("γc") molecule.

The IL-21 receptor gene has been mapped to human chromosome 16p12 (see Parrish-Novak et al., *Nature* 408: 57-63, 2000; Ozaki et al., *Proc. Natl. Acad. Sci. USA* 97:11439-11444, 2000). The IL-21 receptor, which is 538 amino acids in length, is most closely related to human IL-2 beta receptor, and contains a WSXWS motif in the extracellular region, typical of type-1 cytokine receptors. The sequence of the human IL-21 receptor is available as GENBANK® Accession Nos. NM 021798, NM 181079 and NM181078. The mouse sequences are available as NM 021887. The human IL-2Rγc sequence is available as Accession No. MN000206. The mouse IL-2Rγc sequence is available as Accession No. NM013563. These sequences are incorporated herein by reference.

Immunoglobulins: A class of proteins found in plasma and other body fluids that exhibits antibody activity and binds with other molecules with a high degree of specificity; divided into five classes (IgM, IgG, IgA, IgD, and IgE) on the basis of structure and biological activity. The IgG class has been further divided into the IgG1, IgG2a, IgG2b, and IgG3 subtypes. Immunoglobulins and certain variants thereof are known and many have been prepared in recombinant cell culture (e.g. see U.S. Pat. No. 4,745,055; U.S. Pat. No. 4,444,487; WO 88/03565; EP 256,654; EP 120,694; EP 125, 023; Faoulkner et al., *Nature* 298:286, 1982; Morrison, *J. Immunol.* 123:793, 1979; Morrison et al., *Ann Rev. Immunol* 2:239, 1984).

A native (naturally occurring) immunoglobulin is each is made up of four polypeptide chains. There are two long chains, called the "heavy" or "H" chains which weigh between 50 and 75 kilodaltons and two short chains called "light" or "L" chains weighing in at 25 kilodaltons. They are linked together by what are called disulfide bonds to form a "Y" shape molecule. Each heavy chain and light chain can be divided into a variable region and a constant region. An Fc region includes the constant regions of the heavy and the light chains, but not the variable regions.

Isolated: An isolated biological component (such as a nucleic acid, peptide or protein) has been substantially separated, produced apart from, or purified away from other biological components in the cell of the organism in which the component naturally occurs, i.e. other chromosomal and extrachromosomal DNA and RNA, and proteins. Nucleic acids, peptides and proteins that have been isolated include nucleic acids and proteins purified by standard purification methods. The term also embraces nucleic acids, peptides, and proteins prepared by recombinant expression in a host cell as well as chemically synthesized nucleic acids.

Janus Activated kinase (Jak)/Signal Transducer and Activator of Transcription (Stat): Jaks are cytoplasmic tyrosine kinases that are either constitutively associated with cytokine receptors or recruited to receptors after ligand binding. In either case, stimulation with the ligand results in the catalytic activiation of receptor-associated Jaks. This activation results in the tyrosine phosphorylation of cellular substrates, including the Jak-associated cytokine receptor chains. Some of these phosphoylated tyrosines can serve as coding sites for Stat proteins, which bind to the phsphotyrosines by their SRC-homology 2 (SH2) domains. Stat proteins are also phosphylated on a conserved tyrosine residue, resulting in their dimerization and acquisition of high-affintiy DNA-binding activity, which facilitates their action as nuclear transcription factors.

The Jak/Stat pathway is one of the most rapid cytoplasmic to nuclear signaling mechanisms. There are a total of four Jak (Jak1-3 and tyrosine kinase 2) and seven Stat proteins (Stat1-4, Stat5A, Stat5b and Stat6). Jaks are relatively large cytoplasmic kinases of about 1,100 amino acids in length, and range in size from about 116 kDa to about 140 kDa. Binding of IL-21 activates a Jak/Stat signaling pathway. Specifically IL-21 activates Jak1 and Jak3, which then phosphorylate cellular substrates, including one of the IL-21 receptor chains. This allows recruitment of Stat 5A and Stat5B proteins to the phosphorylated receptor by their SH2 domains, which in turn, are also phosphorylated. The Stat proteins can dimerize, translocate to the nucleus, and bind DNA. Binding of the Stat proteins to the DNA results in transcription being activated (for review see Leonard, *Nature Reviews* 1: 200-208, 2001).

Mammal: This term includes both human and non-human mammals. Similarly, the terms "subject," "patient," and "individual" include human and veterinary subjects.

Neutralizing amount: An amount of an agent sufficient to decrease the activity or amount of a substance to a level that is undetectable using standard method.

Nucleic acid: A sequence composed of nucleotides, including the nucleotides that are found in DNA and RNA.

Oligonucleotide: A linear polynucleotide sequence of up to about 200 nucleotide bases in length, for example a polynucleotide (such as DNA or RNA) which is at least 6 nucleotides, for example at least 15, 50, 100 or even 200 nucleotides long.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

Pharmaceutically acceptable carriers: The pharmaceutically acceptable carriers useful with the methods described herein are conventional. *Remington's Pharmaceutical Sci-*

*ences*, by E. W. Martin, Mack Publishing Co., Easton, Pa., 15th Edition (1975), describes compositions and formulations suitable for pharmaceutical delivery of the cytokines and cells disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

PCR (polymerase chain reaction): A method of nucleic acid amplification such as that disclosed in U.S. Pat. Nos. 4,683,195, 4,683,202 and 4,965,188, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e. denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g. hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences can be used to obtain segments of DNA (e.g. genes) for the construction of targeting vectors, transgenes, etc.

As used herein, the terms "PCR product" and "amplification product" refer to the resultant mixture of compounds after two or more cycles of the PCR steps of denaturation, annealing and extension are complete. These terms encompass the case where there has been amplification of one or more segments of one or more target sequences.

Polynucleotide: A linear nucleic acid sequence of any length. Therefore, a polynucleotide includes molecules that are at least 15, 50, 100, 200 (oligonucleotides) and also nucleotides as long as a full-length cDNA.

Probes and primers: A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g. in Sambrook et al., *Molecular Cloning: A Laboratory Manual*, Cold Spring Harbor Laboratory Press (1989); and Ausubel et al., *Current Protocols in Molecular Biology*, Greene Publishing Associates and Wiley-Intersciences (1987).

Primers are short nucleic acids, for example DNA oligonucleotides at least 15 nucleotides in length, and/or no longer than 15, 50, 100 or 200 nucleotides in length. Primers can be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g. by PCR or other nucleic-acid amplification methods known in the art.

Methods for preparing and using probes and primers are described, for example, in Sambrook et al. (*Molecular Cloning: A Laboratory Manual*, Cold Spring Harbor Laboratory Press, 1989), Ausubel et al., *Current Protocols in Molecular Biology*, Greene Publishing Associates and Wiley-Intersciences (1987), and Innis et al., *PCR Protocols, A Guide to Methods and Applications*, 1990, Innis et al. (eds.), 21-27, Academic Press, Inc., San Diego, Calif. PCR primer pairs can be derived from a known sequence, for example, by using computer programs intended for that purpose such as Primer (Version 0.5,© 1991, Whitehead Institute for Biomedical Research, Cambridge, Mass.).

Probes and primers disclosed herein comprise at least 15 nucleotides of a nucleic acid sequence, although a shorter nucleic acid can be used as a probe or primer if it specifically hybridizes under stringent conditions with a target nucleic acid by methods well known in the art. The disclosure thus includes isolated nucleic acid molecules that include specified lengths of the disclosed sequences. One of skill in the art will appreciate that the specificity of a particular probe or primer increases with its length. Thus, for example, a primer comprising 20 consecutive nucleotides of a gene will anneal to a target sequence contained within a genomic DNA library with a higher specificity than a corresponding primer of only 15 nucleotides. To enhance specificity, longer probes and primers can be used, for example probes and primers that comprise at least 20, 30, 40, 50, 60, 70, 80, 90, 100 or more consecutive nucleotides from any region of the disclosed sequences. By way of example, the sequences disclosed herein can be apportioned into halves or quarters based on sequence length, and the isolated nucleic acid molecules can be derived from the first or second halves of the molecules, or any of the four quarters.

When referring to a probe or primer, the term "specific for (a target sequence)" indicates that the probe or primer hybridizes under stringent conditions substantially only to the target sequence in a given sample comprising the target sequence.

Promoter: An array of nucleic acid control sequences which direct transcription of a nucleic acid. A promoter includes necessary nucleic acid sequences near the start site of transcription, such as, in the case of a polymerase II type promoter, a TATA element. In one embodiment, a promoter includes an enhancer. In another embodiment, a promoter includes a repressor element. In these embodiments, a chimeric promoter is created (a promoter/enhancer chimera or a promoter/repressor chimera, respectively). Enhancer and repressor elements can be located adjacent to, or distal to the promoter, and can be located as much as several thousand base pairs from the start site of transcription. Examples of promoters that can be used in the present disclosure include, but are not limited to the SV40 promoter, the CMV enhancer-promoter, the CMV enhancer/pactin promoter, and the tissue-specific promoter probasin.

Other promoter sequences that can be used to practice the methods disclosed herein include, but are not limited to: the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors, any retroviral LTR promoter such as the RSV promoter; inducible promoters, such as the MMTV promoter; the metallothionein promoter; heat shock promoters; the albumin promoter; the histone promoter; the α-actin promoter; TK promoters; B19 parvovirus promoters; the SV10 late promoter; the ApoAI promoter and combinations thereof.

In some embodiments, the promoter is a strong promoter, which promotes transcription of RNA at high levels, for example at levels such that the transcriptional activity of the promoter generally accounts for about 25% of transcriptional activity of all transcription within a cell. The strength of a promoter is often tissue-specific and thus can vary from one cell type to another. For example, CMV is a classic strong promoter because it generates high levels of transcriptional activity in many cell types. Examples of strong promoters include, but are not limited to: CMV; CMV/chicken β-actin; elongation factors 1A and 2A; SV40; RSV; and the MoLV LTR.

In other embodiments, the promoter is a tissue-specific promoter, which promotes transcription in a single cell type or narrow range of tissues. Examples of tissue-specific promoters include, but are not limited to: probasin (which is promotes expression in prostate cells), an immunoglobulin promoter; a whey acidic protein promoter; a casein promoter; glial fibrillary acidic protein promoter; albumin promoter; β-globin promoter; and the MMTV promoter.

In yet other embodiments, the promoter is a hormone-responsive promoter, which promotes transcription only when exposed to a hormone. Examples of hormone-responsive promoters include, but are not limited to: probasin (which is responsive to testosterone and other androgens); MMTV promoter (which is responsive to dexamethazone, estrogen, and androgens); and the whey acidic protein promoter and casein promoter (which are responsive to estrogen).

Purified: The term purified does not require absolute purity or isolation; rather, it is intended as a relative term. Thus, for example, a purified (or isolated) protein preparation is one in which the protein is more pure than the protein in its natural environment within a cell. Such proteins may be produced, for example, by standard purification techniques, or by recombinant expression. In some embodiments, a preparation of a protein is purified such that the protein represents at least 50%, for example at least 70%, of the total protein content of the preparation.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g. by genetic engineering techniques, such as those described in Sambrook et al. (In: *Molecular Cloning: A Laboratory Manual*, Cold Spring Harbor, N.Y., 1989).

Sample: Includes biological samples containing genomic DNA, RNA, or protein obtained from the cells of a subject, such as those present in peripheral blood, urine, saliva, tissue biopsy, surgical specimen, fine needle aspirates, amniocentesis samples and autopsy material.

Selection markers or selectable markers: Refer to the use of a gene that encodes an enzymatic activity that confers resistance to an antibiotic or drug upon the cell in which the selectable marker is expressed. Selectable markers can be "positive"; positive selectable markers typically are dominant selectable markers, i.e. genes that encode an enzymatic activity that can be detected in any mammalian cell or cell line (including ES cells). Examples of dominant selectable markers include, but are not limited to, (1) the bacterial aminoglycoside 3' phosphotransferase gene (also referred to as the neo gene) which confers resistance to the drug G418 in mammalian cells, (2) the bacterial hygromycin G phosphotransferase (hyg) gene which confers resistance to the antibiotic hygromycin and (3) the bacterial xanthine-guanine phosphoribosyl transferase gene (also referred to as the gpt gene) which confers the ability to grow in the presence of mycophenolic acid. Selectable markers can be "negative"; negative selectable markers encode an enzymatic activity whose expression is cytotoxic to the cell when grown in an appropriate selective medium. For example, the HSV-tk gene and the dt gene are commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme. Similarly, the expression of the dt gene selects against cells capable of expressing the Diphtheria toxin. The terms are further defined, and methods further explained, by U.S. Pat. No. 5,464,764.

An animal whose genome "comprises a heterologous selectable marker gene" is an animal whose genome contains a selectable marker gene not naturally found in the animal's genome that is introduced by means of molecular biological methods. A heterologous selectable marker is distinguished from an endogenous gene naturally found in the animal's genome in that expression or activity of the heterologous selectable marker can be selected for or against.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Homologues of an IL-2 receptor polypeptide or a gene encoding an IL-21 receptor polypeptide, will possess a relatively high degree of sequence identity when aligned using standard methods.

Methods of alignment of polypeptide and polynucleotide sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet, et al., *Nucleic Acids Research* 16:10881, 1988; and Pearson and Lipman, *Proc. Natl. Acad. Sci. U.S.A.* 85:2444, 1988. Altschul, et al., *Nature Genet.,* 6:119, 1994 presents a detailed consideration of sequence alignment methods and homology calculations.

The NCBI Basic Local Alignment Search Tool (BLAST) (Altschul, et al., *J. Mol. Biol.* 215:403, 1990) is available from several sources, including the National Center for Biotechnology Information (NCBI, Bethesda, Md.) and on the Internet, for use in connection with the sequence analysis programs blastp, blastn, blastx, tblastn and tblastx. A description of how to determine sequence identity using this program is available on the NCBI website on the internet.

Small Molecule: The term small molecule encompasses a wide variety of chemical compounds, including both inorganic and organic molecules. By definition, a molecule is the smallest unit of matter that can exist by itself while retaining its chemical properties. A macromolecule is a large molecule in which there is a large number of one or several relatively simple structural units, each consisting of several atoms bonded together, e.g., nucleic acids, polypeptides, polysaccharides. In the context of drug development, the term small molecule is used to refer to compounds that are not macromolecules (e.g., biological macromolecules such as nucleic acids, proteins, polypeptides, etc.). A small molecule is typically made up of a single structural and functional unit or a small number of simple structural units. Small molecules are purified or isolated from natural products, or can be produced synthetically. Frequently, small molecules are members of libraries produced by combinatorial chemistry. Typically, a small molecule is less than about 1000 Daltons.

Specific binding agent: An agent that binds substantially only to a defined target. Thus an IL-21 receptor specific binding agent is an agent that binds substantially to an IL-21 receptor. In one embodiment, the specific binding agent is a monoclonal or polyclonal antibody that specifically binds the IL-21 receptor.

The term "specifically binds" refers with respect to an antigen, such as the IL-21 receptor, to the preferential association of an antibody or other ligand, in whole or part, with a cell or tissue bearing that antigen and not to cells or tissues lacking that antigen. It is, of course, recognized that a certain degree of non-specific interaction may occur between a molecule and a non-target cell or tissue. Nevertheless, specific binding may be distinguished as mediated through specific recognition of the receptor or antigen. Although selectively reactive antibodies bind antigen, they may do so with low affinity. On the other hand, specific binding results in a much stronger association between the antibody (or other ligand) and cells bearing the antigen than between the bound antibody (or other ligand) and cells lacking the antigen. Specific binding typically results in greater than 2-fold, preferably greater than 5-fold, more preferably greater than 10-fold and most preferably greater than 100-fold increase in amount of bound antibody or other ligand (per unit time) to a cell or tissue bearing IL-21 receptor as compared to a cell or tissue lacking IL-21 receptor. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, ANTIBODIES, A LABORATORY MANUAL, Cold Spring Harbor Publications, New York (1988), for a description of immunoassay formats and conditions that can be used to determine specific immunoreactivity.

Subject: Living multicellular vertebrate organisms, a category that includes both human and veterinary subjects for example, mammals, birds and primates.

Supernatant: The culture medium in which a cell is grown. The culture medium can include material from the cell. If the cell is infected with a virus, the supernatant can include viral particles.

Targeting vector and Targeting construct: Oligonucleotide sequences that are used in homologous recombination with a chromosomal gene. In one embodiment, a targeting construct includes an IL-21 or an IL-4 gene sequence. The term "IL-21 receptor gene" refers to a gene encoding at least one exon of an IL-21 receptor sequence. The term "IL-4 gene" refers to a gene encoding at least one exon of an IL-4 sequence. The targeting vector can also include a selectable marker gene. In one embodiment, the targeting vector contains genomic sequences flanking two exons of the IL-21 receptor gene sufficient to permit the homologous recombination of the targeting vector into the IL-21 receptor gene resident in the chromosomes of the target or recipient cell (e.g., ES cells). In another embodiment, the targeting vector contains genomic sequences flanking two exons of the IL-4 gene sufficient to permit the homologous recombination of the targeting vector into the IL-4 gene resident in the chromosomes of the target or recipient cell (e.g., ES cells).

Typically, though not necessarily, the targeting vector contains 2 kb to 50 kb of DNA homologous to the IL-4 or the IL-21 receptor gene. In one embodiment, the targeting vector contains 8-20 kb of DNA homologous to the IL-4 or the IL-21 receptor gene. In another embodiment, the targeting vector contains about 10 Kb of DNA homologous to the IL-4 or the IL-21 receptor gene.

This homologous DNA can be located downstream or upstream of the selectable marker gene, or can be divided on each side of the selectable marker gene. In one embodiment, the selectable marker gene is located upstream of the IL-4 or the IL-21 receptor gene. The targeting vector can contain more than one selectable maker gene. When more than one selectable marker gene is employed, the targeting vector can contain both a positive selectable marker (e.g. the neo gene) and a negative selectable marker (e.g. the Herpes simplex virus tk (HSV-tk) gene). The presence of the positive selectable marker permits the selection of recipient cells containing an integrated copy of the targeting vector whether this integration occurred at the target site or at a random site. The presence of the negative selectable marker permits the identification of recipient cells containing the targeting vector at the targeted site (i.e. which has integrated by virtue of homologous recombination into the target site); cells which survive when grown in medium that selects against the expression of the negative selectable marker do not contain a copy of the negative selectable marker.

The targeting vectors of the present disclosure are of the "replacement-type;" integration of a replacement-type vector results in the insertion of a selectable marker into the target gene. As demonstrated herein, replacement-type targeting vectors can be employed to disrupt a gene, resulting in the generation of a null allele (i.e. an allele incapable of expressing a functional protein; null alleles can be generated by deleting a portion of the coding region, deleting the entire gene, introducing an insertion and/or a frameshift mutation, etc.) or can be used to introduce a modification (e.g., one or more point mutations) into a gene.

Therapeutically Effective Amount: An amount sufficient to achieve a desired biological effect, for example an amount that is effective to affect the production of immunoglobulins. In particular examples, it is an amount of an agent effective to inhibits the interaction of IL-21 with its receptor, such as in a subject to whom it is administered, such as a subject undergoing an allergic reaction. In another particular example, a therapeutically effective amount is an amount of IL-21 that alters a sign or a symptom of a disorder in a subject, such as the production of IgE in a subject that has Job's disease.

In one embodiment, the therapeutically effective amount also includes a quantity of to achieve a desired effect in a subject being treated. For instance, these can be an amount necessary to improve signs and/or symptoms a disease such as Job's disease or an allergic response, for example by altering the production of an immunoglobulin.

An effective amount of an agent that inhibits the interaction of IL-21 with its receptor can be administered in a single dose, or in several doses, for example daily, during a course of treatment. However, the effective amount of an agent that inhibits the interaction of IL-21 with its receptor will be dependent on the subject being treated, the severity and type of the condition being treated, and the manner of administration. For example, a therapeutically effective amount of purified. The methods disclosed herein have equal application in medical and veterinary settings. Therefore, the general term "subject being treated" is understood to include all organisms (e.g. humans, apes, dogs, cats, horses, and cows) that require an increase in the desired biological effect, such as an enhanced immune response.

Transduced and Transformed: A virus or vector transduces or transfects a cell when it transfers nucleic acid into the cell. A cell is "transformed" by a nucleic acid transduced into the cell when the DNA becomes stably replicated by the cell, either by incorporation of the nucleic acid into the cellular genome, or by episomal replication. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Transgene: A foreign gene that is placed into an organism by introducing the foreign gene into embryonic stem (ES) cells, newly fertilized eggs or early embryos. In one embodiment, a transgene is a gene sequence, for example a sequence that encodes a marker polypeptide that can be detected using methods known to one of skill in the art. In another embodiment, the transgene encodes a therapeutic polypeptide that can be used to alleviate or relieve a symptom of a disorder. In yet another embodiment, the transgene encodes a therapeutically effective oligonucleotide, for example an antisense oligonucleotide, wherein expression of the oligonucleotide inhibits expression of a target nucleic acid sequence. In a further embodiment, the transgene encodes an antisense nucleic acid or a ribozyme. In yet another embodiment, a transgene is a stop cassette.

In other embodiments, a transgene contains native regulatory sequences operably linked to the transgene (e.g. the wild-type promoter, found operably linked to the gene in a wild-type cell). Alternatively, a heterologous promoter can be operably linked to the transgene. In yet another embodiment, a viral LTR can be used to express the transgene.

Transgenic Cell: Transformed cells that contain foreign, non-native DNA.

Transgenic Animal: An animal, for example, a non-human animal such as a mouse, that has had DNA introduced into one or more of its cells artificially. By way of example, this is commonly done by random integration or by targeted insertion. DNA can be integrated in a random fashion by injecting it into the pronucleus of a fertilized ovum. In this case, the DNA can integrate anywhere in the genome, and multiple copies often integrate in a head-to-tail fashion. There is no need for homology between the injected DNA and the host genome.

Targeted insertion, the other common method of producing transgenic animals, is accomplished by introducing the DNA into embryonic stem (ES) cells and selecting for cells in which the DNA has undergone homologous recombination with matching genomic sequences. For this to occur, there often are several kilobases (kb) of homology between the exogenous and genomic DNA, and positive selectable markers are often included. In addition, negative selectable markers are often used to select against cells that have incorporated DNA by non-homologous recombination (random insertion).

Vector: A nucleic acid molecule as introduced into a cell, thereby producing a transformed cell. A vector can include nucleic acid sequences that permit it to replicate in the cell, such as an origin of replication. A vector can also include one or more marker or therapeutic transgenes and other genetic elements known in the art.

In some embodiments, the vector is a non-viral vector, such as a bacterial vector. In other embodiments, the vector is a viral vector. Examples of viral vectors include, but are not limited to adenoviral vectors, retroviral vectors, and Herpes viral vectors.

Wild-type: The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and/or functional properties (i.e. altered characteristics) when compared to the wild-type gene or gene product. It is noted that naturally-occurring mutants can be isolated; these are typically identified by the fact that they have altered characteristics when compared to the wild-type gene or gene product.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Production of a Knock-Out Mouse

A transgenic mouse is disclosed herein whose somatic and germ cells comprise a disrupted IL-21 receptor gene, the disruption being sufficient to diminish or inhibit the binding of IL-21 to the cell surface. For example, the disruption in the IL-21 receptor gene can be such that a polypeptide encoded by the IL-21 receptor gene (or a subportion thereof), which is disrupted with respect to IL-21 ligand binding is expressed at the cell surface. Alternatively, the disruption in the IL-21 receptor gene can be such that transcription and/or translation and/or incorporation at the cell surface is impaired. The transgenic mouse can comprise a disrupted IL-21 receptor, and a disrupted IL-4 gene. The disruption of IL-4 is sufficient to inhibit the production of IL-4 or the binding of IL-4 to the IL-4 receptor. Mice that are IL-4$^{-/-}$IL-21$^{-/-}$, IL-4$^{-/-}$IL-21R$^{-/-}$, IL-4$^{-/-}$IL-21$^{-/-}$, that have a decreased B cell activity are also encompassed by this disclosure. One of skill in the art, using the description provided herein, can readily produce these animals. In one embodiment, these mice exhibit decreased immunoglobulin production, such as decreased IgG or IgE production.

A DNA molecule containing a desired gene sequence, such as an IL-4 gene sequence or an IL-21 receptor gene sequence can be introduced into pluripotent cells (such as ES cells) by any method that will permit the introduced molecule to undergo recombination at its regions of homology. Techniques that can be used include calcium phosphate/DNA co-precipitates, microinjection of DNA into the nucleus, electroporation, bacterial protoplast fusion with intact cells, transfection, polycations, e.g., polybrene, polyornithine, etc. The DNA can be single or double stranded DNA, linear or circular. Techniques for transforming mammalian cells are known, and examples for such methods are described, for instance, in Keown et al., *Meth. Enzym.* (1989), Keown et al., *Meth. Enzym.* Vol. 185, pp. 527-537, 1990 and Mansour et al., *Nature*, 336:348-352, 1988.

Some methods, such as direct microinjection, or calcium phosphate transformation, may cause the introduced nucleic acid molecule to form concatemers upon integration. These concatemers can resolve themselves to form non-concatemeric integration structures. An alternative method for introducing the gene to the pluripotent cell is electroporation (Toneguzzo, et al., *Nucleic Acids Res.* 16:5515-5532, 1988; Quillet et al., *J. Immunol.* 141:17-20, 1988; Machy et al., *Proc. Natl. Acad. Sci. USA* 85:8027-8031, 1988).

After introduction of the DNA molecule(s), the cells are usually cultured under conventional conditions, as are known in the art. A selectable marker (as discussed above) can be used to facilitate the recovery of those cells that have received the DNA molecule containing the desired gene sequence. For the purposes of the present disclosure, any gene sequence whose presence in a cell permits recognition and clonal isolation of the cell can be employed as a detectable marker, whether or not it conveys a survival advantage in the transgenic cell.

After selection for cells that have incorporated the desired DNA molecule, the cells are cultured, and the presence of the introduced DNA molecule is confirmed as described above. For instance, approximately $10^7$ cells are cultured and screened for cells that have undergone a second recombinational event (discussed below), resulting in the replacement of a native sequence (i.e. a gene sequence that is normally and naturally present in the recipient cell) with the desired gene sequence. Any of a variety of methods can be used to identify cells that have undergone the second recombinational event, including direct screening of clones, use of PCR, use of hybridization probes, etc.

In one embodiment, a gene is located upstream or downstream from the targeting construct that provides for identification of whether a double crossover (and therefore targeted integration, not random integration) has occurred. By way of example, the herpes simplex virus thymidine kinase (HSV-tk) gene can be employed for this purpose, since the presence of the thymidine kinase gene is detected by the use of nucleoside analogs, such as acyclovir or gangcyclovir, for their cytotoxic effects on cell that contain a functional HSV-tk gene. The absence of sensitivity to these nucleoside analogs indicates the absence of the thymidine kinase and indicates that, therefore, where homologous recombination has occurred, a double crossover event has also occurred.

Once the DNA molecule containing the construct has been introduced into the ES cells (or other pluripotent cells), the construct recombines with the wild-type IL-4 gene or the IL-21 receptor gene through the process of homologous recombination. Homologous recombination provides a method for introducing a desired gene sequence into a plant or animal cell and producing chimeric or transgenic plants and animals having defined, and specific, gene alterations. A discussion of the process of homologous recombination can be found in Watson, J. D., In: *Molecular Biology of the Gene,* 3rd Ed., W. A. Benjamin, Inc., Menlo Park, Calif. (1977).

In brief, homologous recombination is a well-studied natural cellular process that results in the scission of two nucleic acid molecules having identical or substantially similar sequences (i.e. "homologous"), and the ligation of the two molecules such that one region of each molecule initially present is now ligated to a region of the other initially present molecule (Sedivy, *Bio-Technol.* 6:1192-1196, 1988). Homologous recombination is a sequence-specific process by which cells can transfer a "region" of DNA from one DNA molecule to another. As used herein, a "region" of DNA is intended to generally refer to any nucleic acid molecule. The region can be of any length from a single base to a substantial fragment of a chromosome, and can, but needs not, include coding regions for one or more proteins.

For homologous recombination to occur between two DNA molecules, the molecules can possess a "region of homology" with respect to one another. Such a region of homology is usually at least two base pairs long, but is more customarily 2-20 Kb long. Two DNA molecules possess such a "region of homology" when one contains a region whose sequence is so similar to a region in the second molecule that base pairing and homologous recombination can occur. Recombination is usually catalyzed by enzymes that are naturally present in both prokaryotic and eukaryotic cells.

The transfer of a region of DNA can be envisioned as occurring through a multi-step process (see published PCT Application No. WO 02/14495 A2). If either of the two participant nucleic acid molecules is circular, then a recombination event results in the integration of the circular molecule into the other participant nucleic acid molecule. Importantly, if a particular region is flanked on both sides by regions of homology (which can be the same, but can also be different), then two recombinational events can occur, thus resulting in the exchange of a region of DNA between two DNA molecules. Recombination can be "reciprocal,"

and thus result in an exchange of DNA regions between two recombining DNA molecules. Alternatively, it can be "nonreciprocal" (also referred to as "gene conversion") and result in both recombining nucleic acid molecules having the same nucleotide sequence.

For homologous recombination, constructs are prepared where the gene of interest is flanked on one or both sides with DNA homologous with the DNA of the target region. The homologous DNA is generally within 100 kb, but can be within 50 kb, 25 kb, or, in some embodiments, about 2.5 kb or 1.5 kb or more of the target gene. The homologous DNA can include the 5'-upstream region comprising any enhancer sequences, transcriptional initiation sequences, the region 5' of these sequences, or the like. The homologous region can include a portion of the coding region, where the coding region of a gene can include an open reading frame or combination of exons and introns. The homologous region can comprise all or a portion of an intron, where all or a portion of one or more exons also can be present.

Alternatively, the homologous region can comprise the 3'-region, so as to comprise all or a portion of the transcription termination region of a gene, or the region 3' thereof. The homologous regions can extend over all or a portion of a target gene, or be outside the target gene but include all or a portion of the transcriptional regulatory regions of the structural gene. In many embodiments, the homologous sequence will be joined to the gene of interest, proximally or distally. Usually, a sequence other than the wild-type sequence normally associated with the target gene will be used to separate the homologous sequence from the gene of interest on at least one side of the gene of interest. Some portion of the sequence can be the 5' or 3' sequence associated with the gene of interest (the target).

In order to prepare the subject recombining constructs, it is necessary to know the sequence that is targeted for homologous recombination. While a sequence of 14 bases complementary to a sequence in a genome can provide for homologous recombination, normally the individual flanking sequences will be at least about 150 bp, and can be 12 kb or more, but usually not more than about 8 kb. The size of the flanking regions are determined by the size of the known sequence, the number of sequences in the genome which can have homology to the site for integration, whether mutagenesis is involved and the extent of separation of the regions for mutagenesis, the particular site for integration, or the like.

In one embodiment, a targeting vector is utilized for functionally disrupting an endogenous IL-4 gene or IL-21 receptor gene in a cell includes:

a) a nonhomologous replacement portion;
b) a first homology region located upstream of the nonhomologous replacement portion, the first homology region having a nucleotide sequence with substantial identity to a first IL-4 or IL-21 receptor gene sequence; and
c) a second homology region located downstream of the nonhomologous replacement portion, the second homology region having a nucleotide sequence with substantial identity to a second IL-4 or IL-21 receptor gene sequence, the second IL-4 or IL-21 receptor gene sequence having a location downstream of the first IL-4 or IL-21 receptor gene sequence in a naturally occurring endogenous IL-4 or IL-21 receptor gene.

Thus, the nonhomologous replacement portion is flanked 5' and 3' by nucleotide sequences with substantial identity to an IL-4 or an IL-21 receptor gene sequences. A nucleotide sequence with "substantial identity" to an IL-4 or an IL-21 receptor gene sequence is intended to describe a nucleotide sequence having sufficient homology to an IL-4 or an IL-21 receptor gene sequence to allow for homologous recombination between the nucleotide sequence and an endogenous IL-4 or IL-21 receptor gene sequence in a host cell. Typically, the nucleotide sequences of the flanking homology regions are at least 90%, more preferably at least 95%, even more preferably at least 98% and most preferably 100% identical to the nucleotide sequences of the endogenous IL-4 or IL-21 receptor gene to be targeted for homologous recombination. In one embodiment, the flanking homology regions are isogenic with the targeted endogenous allele (e.g., the DNA of the flanking regions is isolated from cells of the same genetic background as the cell into which the targeting construct is to be introduced). Additionally, the flanking homology regions of the targeting vector are of sufficient length for homologous recombination between the targeting vector and an endogenous IL-4 or an IL-21 receptor gene in a host cell when the vector is introduced into the host cell. Typically, the flanking homology regions are at least 1 kilobase in length and more preferably are least several kilobases in length.

Chimeric or transgenic animals are prepared, for example, by introducing a IL-21 receptor or an IL-4 construct, as described herein, into a precursor pluripotent cell, such as an ES cell, or equivalent, as described above, and in Robertson, E. J., In: *Current Communications in Molecular Biology*, Capecchi, M. R. (ed.), Cold Spring Harbor Press, Cold Spring Harbor, N.Y., 1989, pp. 39-44. The term "precursor" is intended to denote only that the pluripotent cell is a precursor to the desired ("transfected") pluripotent cell that is prepared in accordance with the teachings of the present disclosure. The pluripotent (precursor or transfected) cell can be cultured in vivo, in a manner known in the art (Evans et al., *Nature* 292:154-156, 1981) to form a chimeric or transgenic animal.

Any ES cell can be used in accordance with the present disclosure. For instance, in some embodiments, primary isolates of ES cells are used. Such isolates can be obtained directly from embryos such as the CCE cell line disclosed by Robertson, E. J., In: *Current Communications in Molecular Biology*, Capecchi, M. R. (ed.), Cold Spring Harbor Press, Cold Spring Harbor, N.Y. (1989), pp. 39-44), or from the clonal isolation of ES cells from the CCE cell line (Schwartzberg, et al., *Science* 246:799-803, 1989). Such clonal isolation can be accomplished according to the method of E. J. Robertson (In: *Teratocarcinomas and Embryonic Stem Cells: A Practical Approach* (E. J. Robertson, Ed.), IRL Press, Oxford, 1987). The purpose of such clonal propagation is to obtain ES cells that have a greater efficiency for differentiating into an animal. Examples of ES cell lines that have been clonally derived from embryos are the ES cell lines, AB1 (hprt+) or AB2.1 (hprt−).

The ES cells can be cultured on stromal cells (such as STO cells (especially SNC4 STO cells) and/or primary embryonic fibroblast cells) as described by E. J. Robertson (In: *Teratocarcinomas and Embryonic Stem Cells: A Practical Approach*, (E. J. Robertson, Ed.), IRL Press, Oxford, 1987, pp. 71-112). The stomal (and/or fibroblast) cells serve to eliminate the clonal overgrowth of abnormal ES cells. The cells can be cultured in the presence of leukocyte inhibitory factor ("LIF") (Gough et al., *Reprod. Fertil. Dev.* 1:281-288, 1989; Yamamori et al., *Science* 246:1412-1416, 1989). Since the gene encoding LIF has been cloned (Gough et al., *Reprod. Fertil. Dev.* 1:281-288, 1989), it is also possible to transform stomal cells with this gene, by methods known in the art, and to then culture the ES cells on transformed stomal cells that secrete LIF into the culture medium.

ES cell lines can be derived or isolated from any species (for example, chicken, etc.), including cells derived or isolated from mammals such as rodents (i.e. mouse, rat, hamster, etc.), rabbits, sheep, goats, fish, pigs, cattle, and primates such as humans. In one embodiment, the mammal is a mouse.

Transformed ES cells then can be injected into blastocysts. Blastocysts containing the targeted ES cells are implanted into pseudo-pregnant females and allowed to develop to term. The ES cells thereafter colonize the embryo and can contribute to the germ line of the resulting chimeric animal (Jaenisch, Science 240:1468-1474, 1988). Chimeric offspring are identified, for instance, by coat-color markers, and those showing chimerism are selected for breeding offspring. Those offspring that carry the mutant allele can be identified by coat color or other markers, and the presence of the mutant allele reaffirmed by DNA analysis of blood samples.

A "double knock-out" can be generated by introducing two constructs into a single ES cell, one designed to undergo homologous recombination with the endogenous (wild-type) IL-4 gene, and one designed to undergo homologous recombination with the endogenous (wild-type) IL-21 receptor gene. Alternatively, one line of mice can be generated that is homozygous for an IL-4 gene deletion (knock-out). An additional line of mice can be generated that is homozygous for an IL-21 receptor gene deletion (knock-out). These two lines of mice can then be mated to produce mice that have both the IL-4 and the IL-21 receptor genes deleted.

In another embodiment, a line of mice can be generated that is homozygous for an IL-4 gene deletion. These animals are mated, and blastocysts are collected. Embryonic stem cells are then prepared from the IL-4$^{-/-}$ mice, and a construct is introduced into these cells designed to undergo homologous recombination with the IL-21 receptor gene. Resultant offspring are mated and IL-4$^{-/-}$IL-21receptor (R)$^{-/-}$ mice are selected. In another embodiment, a line of mice can be generated that is homozygous for an IL-21 receptor gene deletion. These animals are mated, and blastocysts are collected from the IL-21R$^{-/-}$ mice. Embryonic stem cells are then prepared from the IL-21$^{-/-}$ mice, and a construct is introduced into these cells designed to undergo homologous recombination with the IL-4 gene.

In addition to using homologous recombination in ES cells to produce gene knock-outs, a recombining site/recombinase system can be used to generate knock-out genes (Rajewsky, J. Clin. Invest. 98:600-603, 1996). The Cre enzyme is a member of a large family of recombinases that recognizes specifically recombining sites (e.g. loxP, a sequence motif of 34 base pairs) and can induce recombination at these sites. If a DNA segment is flanked by two loxP sites in the same orientation, Cre excises that segment from the DNA, leaving a single LoxP behind. By appropriately positioning the two loxP sites, this system can be used to generate deletions, such as a deletion in an IL-21 receptor, IL-21, IL-4 receptor, or IL-4 gene.

Thus, in one embodiment, a transgenic mouse is produced that includes a loxP flanked (floxed) gene, such as an IL-21 receptor, IL-21, IL-4 receptor, or IL-4 gene. Mice are also produced that include a promoter, such as a tissue specific (e.g. an immunoglobulin promoter) or an inducible promoter (e.g. a temperature sensitive promoter), operably linked to Cre gene in their genome. Mice including the floxed gene are then mated to the mice including the Cre gene. Under appropriate conditions, the expression of Cre is induced, and recombination occurs at the recombining sites, resulting in deletion of the floxed gene, such as the IL-4, IL-4 receptor, IL-21, or IL-21 receptor gene. Alternative recombinase systems (such as the flp recombinase) can also be employed for the purpose of creating targeted mutations in the IL-21 gene, the IL-21 receptor gene, the IL-4 gene and/or the IL-4 receptor gene.

In one embodiment, IL4$^{-/-}$IL-21R$^{-/-}$ mice exhibit decreased IgE production. In one embodiment, the IgE production is decreased at least about 40%, 50%, 60%, 70%, 80%, 90%, 95%, or 99% as compared to a control. In one embodiment, a control is an IL-4$^{+/+}$IL-21R$^{+/+}$ (wild-type) animal. In another embodiment, a control is a standard value.

In one embodiment, IL4$^{-/-}$IL-21R$^{-/-}$ mice exhibit decreased IgG production. Thus, the IgG production (for example, IgG1, IgG2a, IgG2b, or IgG3) is decreased at least about 40%, 50%, 60%, 70%, 80%, 90%, 95%, or 99% as compared to a control. In a further embodiment, IL4$^{-/-}$IL-21$^{-/-}$ mice exhibit decreased IgM production. Thus, the IgM production is decreased at least about 40%, 50%, 60%, 70%, 80%, or 90% as compared to a control, such as a wild-type animal or a standard value. In a further embodiment, IL4$^{-/-}$IL-21$^{-/-}$ mice exhibit pan-hypogammaglobulinemia (a decrease in production of all immunoglobulins).

In one embodiment, IL4$^{-/-}$IL-21R$^{-/-}$ mice are used to test agents designed to affect immunoglobulin secretion. Thus, and agent is administered to an IL4$^{-/-}$IL-21R$^{-/-}$ mice, and its effect on immunoglobulin production is assessed. In one embodiment, the production of a specific immunoglobulin, such as IgE, IgG1, IgG2a, IgG2b, or IgG3 is assessed.

Methods of Altering a B Cell Activity

As disclosed herein, decreased interaction of IL-21 with its receptor can cause a reduction in a B cell activity. Upon binding of to a functional IL-21 receptor (IL-21R/IL-2Rγc (γc) heterodimer), IL-21 induces intracellular signaling by pathways including the Jak/Stat pathway. Although IL-21 is capable of binding to the IL-21R in the absence of γc, the γc is involved in transducing the intracellular signal induced by IL-21. Binding of IL-21 to the IL-21/γc heterdimer results in phosphorylation of the Janus kinase 1 (Jak 1). Depending on cell type, signaling through the IL-21R/γc heterdimer complex activates overlapping subsets of the downstream targets Jak1, Jak3, Stat1, Stat3, Stat4 and Stat 5. Activation of these downstream targets produces a diverse range of physiological responses mediated via IL-21 induced signaling. Additional details regarding IL-21/IL-21R signaling can be found in, e.g., Kovanen and Leonard Immunological Reviews 202:67-83, 2004 and Mehta et al., (2004) Immunological Reviews 202:84-95, 2004.

In one embodiment, the B cell activity is the production of an immunoglobulin. The B cell activity can include production of an immunoglobulin class or subclass including IgA, IgE, IgM and IgG. For example, in a human the B cell activity can include production of an immunoglobulin that is an IgA, an IgE, and IgM and an IgG1, IgG2, IgG3 and/or IgG4 immunoglobulin. A mouse B cell activity includes production of, e.g., an IgA, an IgM, an IgE and an IgG1, IgG2a, IgG2b, and/or IgG3 immunoglobulin. Thus, a method is provided for decreasing a B cell activity, including contacting the B cell with an agent (for example, an antagonist) that inhibits the interaction of IL-21 with the IL-21 receptor. In one embodiment, the agent that decreases a B cell activity decreases activation of the Jak/Stat signaling pathway. The B cell can be in vitro or in vivo.

In one embodiment an agent that decreases the activity, for example by decreasing the interaction of IL-21 with its receptor and/or by decreasing activation of IL-21 induced signaling, is an antibody that specifically binds IL-21 or the IL-21 receptor. The IL-21 receptor or a fragment or conservative variant thereof can be used to produce antibodies which are immunoreactive or bind to epitopes of IL-21 or its receptor. In one embodiment, the antibody is a "blocking" or "neutralizing" antibody that binds to IL-21 and inhibits its interaction with its receptor. In another embodiment, the antibody is a neutralizing antibody that binds to the IL-21 receptor on a B cell, and inhibits the interaction of IL-21 with the IL-21 receptor on the B cell.

Polyclonal antibodies, antibodies which consist essentially of pooled monoclonal antibodies with different epitopic specificities, as well as distinct monoclonal antibody preparations are included.

The preparation of polyclonal antibodies is well known to those skilled in the art. See, for example, Green et al., "Production of Polyclonal Antisera," in: *Immunochemical Protocols*, pp. 1-5, Manson, ed., Humana Press 1992; Coligan et al., "Production of Polyclonal Antisera in Rabbits, Rats, Mice and Hamsters," in: *Current Protocols in Immunology*, section 2.4.1, 1992.

The preparation of monoclonal antibodies likewise is conventional. See, for example, Kohler & Milstein, *Nature* 256:495, 1975; Coligan et al., sections 2.5.1-2.6.7; and Harlow et al., in: *Antibodies: a Laboratory Manual*, page 726, Cold Spring Harbor Pub., 1988. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1-2.7.12 and sections 2.9.1-2.9.3; Barnes et al., "Purification of Immunoglobulin G (IgG)," in: *Methods in Molecular Biology*, Vol. 10, pages 79-104, Humana Press, 1992.

Methods of in vitro and in vivo production of monoclonal antibodies are well known to those skilled in the art. Production in vitro may be carried out in suitable culture media such as Dulbecco's Modified Eagle Medium or RPMI 1640 medium, optionally supplemented by a mammalian serum such as fetal calf serum or trace elements and growth-sustaining supplements such as normal mouse peritoneal exudate cells, spleen cells, thymocytes or bone marrow macrophages. Production in vitro provides relatively pure antibody preparations and allows scale-up to yield large amounts of the desired antibodies. Large-scale hybridoma cultivation can be carried out by homogenous suspension culture in an airlift reactor, in a continuous stirrer reactor, or in immobilized or entrapped cell culture. Production in vivo may be carried out by injecting cell clones into mammals histocompatible with the parent cells, e.g., syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Antibodies can also be derived from subhuman primate antibody. General techniques for raising therapeutically useful antibodies in baboons can be found, for example, in Goldenberg et al., International Patent Publication WO 91/11465, 1991, and Losman et al., *Int. J. Cancer* 46:310, 1990.

Alternatively, an antibody that specifically binds IL-21 or its receptor can be derived from a humanized monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Natl. Acad. Sci. USA* 86:3833, 1989. Techniques for producing humanized monoclonal antibodies are described, for example, by Jones et al., *Nature* 321:522, 1986; Riechmann et al., *Nature* 332:323, 1988; Verhoeyen et al., *Science* 239:1534, 1988; Carter et al., *Proc. Natl. Acad. Sci. USA* 89:4285, 1992; Sandhu, *Crit. Rev. Biotech.* 12:437, 1992; and Singer et al., *J. Immunol.* 150:2844, 1993.

Antibodies can be derived from human antibody fragments isolated from a combinatorial immunoglobulin library. See, for example, Barbas et al., in: *Methods: a Companion to Methods in Enzymology*, Vol. 2, page 119, 1991; Winter et al., *Ann. Rev. Immunol.* 12:433, 1994. Cloning and expression vectors that are useful for producing a human immunoglobulin phage library can be obtained, for example, from STRATAGENE Cloning Systems (La Jolla, Calif.).

In addition, antibodies can be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13, 1994; Lonberg et al., *Nature* 368:856, 1994; and Taylor et al., *Int. Immunol.* 6:579, 1994.

Antibodies include intact molecules as well as fragments thereof, such as Fab, F(ab')$_2$, and Fv which are capable of binding the epitopic determinant. These antibody fragments retain some ability to selectively bind with their antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody (SCA), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual*, Cold Spring Harbor Laboratory, New York, 1988). An epitope is any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. No. 4,036,945 and U.S. Pat. No. 4,331,647, and references contained therein. See also Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of V$_H$ and V$_L$ chains. This association may be noncovalent, as described in Inbar et al., *Proc. Natl. Acad. Sci. USA* 69:2659, 1972. Alternatively, the variable chains can be linked by an intermolecular disulfide bond or cross-linked by chemicals such as glutaraldehyde. See, e.g., Sandhu, supra. Preferably, the Fv fragments comprise V$_H$ and V$_L$ chains connected by a peptide linker. These single-chain antigen binding proteins (sFv) are prepared by constructing a structural gene comprising DNA sequences encoding the V$_H$ and V$_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., Methods: a Companion to Methods in Enzymology, Vol. 2, page 97, 1991; Bird et al., *Science* 242:423-426, 1988; Ladner et al., U.S. Pat. No. 4,946,778; Pack et al., *Bio/Technology* 11: 1271-77, 1993; and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., Methods: a Companion to Methods in Enzymology, Vol. 2, page 106, 1991.

Antibodies can be prepared using an intact polypeptide or fragments containing small peptides of interest as the immunizing antigen. The polypeptide or a peptide used to immunize an animal can be derived from substantially purified polypeptide produced in host cells, in vitro translated cDNA, or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, a hamster, a goat or a rabbit).

Polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan et al., Unit 9, Current Protocols in Immunology, Wiley Interscience, 1991).

It is also possible to use the anti-idiotype technology to produce monoclonal antibodies which mimic an epitope. For example, an anti-idiotypic monoclonal antibody made to a first monoclonal antibody will have a binding domain in the hypervariable region that is the "image" of the epitope bound by the first mono-clonal antibody.

In another embodiment, the agent that decreases activity (for example, by inhibiting interaction of IL-21 with the IL-21 receptor and/or by inhibiting activation of signaling induced by IL-21 via the Jak/Stat pathway) is a small inhibitory RNA (see Fui et al., *Proc. Natl. Acad. Sci.* 99: 5515-5520, 2002; Brummelkamp et al., *Science* 296:550-553, 2003, which are both incorporated by reference) or an anti-sense nucleic acid that specifically binds a nucleic acid encoding IL-21 or the IL-21 receptor is introduced into the B cell. The natural mechanism for producing proteins in living cells starts with the DNA being transcribed into RNA. The resulting RNA molecule is then translated into a protein. This chain of events (DNA→RNA→Protein) allows for the regulation of the protein at three different levels. At the first level of regulation the DNA can be targeted. This is done such that the process of making the RNA is inhibited. For example, a small circular oligonucleotide molecule can be placed in contact with the DNA thus inhibiting and/or altering transcription (Wolf, *Nature Biotechnology* 16:341-344, 1998). At the next level the transcription of the RNA can be inhibited. This can be done through the use of complementary polynucleotide sequences that bind to the target RNA molecule. In some instances these polynucleotide molecules can be designed so that they are catalytic. In other words, they can be designed so that they can bind to a first target RNA, cleave it, and then move on to cleave a second RNA.

To inhibit the translation of the target RNA molecule, the antisense molecule must persist in the cell for a sufficient period to contact the target RNA. However, the cell contains enzymes and other components that cause polynucleotide (such as the antisense molecule) to degrade. It is therefore often desirable to engineer the antisense molecule to not be degraded in the cell. This can be done, for example, by substituting the normally occurring phosphodiester linkage that connects the individual bases of the antisense molecule with modified linkages. These modified linkages may, for example, be a phosphorothioate, methylphosphonate, phosphodithioate, or phosphoselenate. Furthermore, a single antisense molecule may contain multiple substitutions in various combinations.

The antisense molecule can also be designed to contain different sugar molecules. For example the molecule may contain the sugars ribose, deoxyribose or mixtures thereof, which are linked to a base. The bases give rise to the molecules' ability to bind complementarily to the target RNA. Complementary binding occurs when the base of one molecule forms a hydrogen bond with another molecule. Normally the base Adenine (A) is complementary to thymidine (T) and uracil (U), while cytosine (C) is complementary to guanine (G). Therefore, the sequence ATCG of the antisense molecule will bond to TAGC of the target RNA. Additionally, in order to be effective the antisense molecule does not have to be 100% complementary to the target RNA.

Catalytic nucleic acid molecules must also contain regions that complement the target RNA sequence. These regions serve to allow the molecules to specifically bind to the target RNA of interest. The catalytic molecules also will contain regions which are not complementary to the target RNA. These non-complementary regions typically will contain a sequence which gives the molecule its catalytic activity. Additionally, the catalytic molecules are subject to the same potential problem of degradation as the antisense molecules. Therefore, the catalytic molecules can be designed to contain the same substitutions already discussed.

The antisense polynucleotides which include both antisense molecules and catalytic nucleic acid molecules, can vary in length. Generally, a longer complementary region will give rise to a molecule with higher specificity. However, these longer molecules tend to be harder to produce synthetically. Therefore, the longer polynucleotide molecules are most often used in conjunction with systems which produce the therapeutic molecules in vivo. These systems involve cloning the polynucleotide sequence into a vector and then delivering the vector to a host cell. The host cell then supplies the necessary components for transcription of the therapeutic molecule.

Shorter polynucleotide (oligonucleotides) can conveniently be produced synthetically as well as in vivo. These IL-21 or IL-21 receptor antisense nucleic acids are of at least six nucleotides, and in particular embodiments are oligonucleotides ranging from 6 to about 50 oligonucleotides. In specific aspects, the oligonucleotide is at least 10 nucleotides, at least 15 nucleotides, at least 100 nucleotides, or at least 200 nucleotides. The oligonucleotides can be DNA or RNA, or chimeric mixtures or derivatives or modified versions thereof, single-stranded or double-stranded. The oligonucleotide can be modified at the base moiety, sugar moiety, or phosphate backbone, and may include other appending groups such as peptides, or agents facilitating transport across the cell membrane (see, e.g., Letsinger et al., *Proc. Natl. Acad. Sci. USA* 86:6553-6556, 1989; Lemaitre et al., *Proc. Natl. Acad. Sci. USA* 84:648-652, 1987; PCT Publication No. WO 88/09810) or blood-brain barrier (see, e.g., PCT Publication No. WO 89/10134), hybridization triggered cleavage agents (see, e.g., Krol et al., *BioTechniques* 6:958-976, 1988) or intercalating agents (see, e.g., Zon, *Pharm. Res.* 5:539-549, 1988).

In one embodiment, an IL-21 or IL-21 receptor antisense polynucleotide is utilized, for example a single-stranded DNA. In a more particular aspect, such a polynucleotide comprises a sequence antisense to the sequence encoding the IL-21 receptor extracellular region. The oligonucleotide may be modified at any position on its structure with substituents generally known in the art. For example, a modified base moiety may be 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N~6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, and 2,6-diaminopurine.

In another embodiment, the polypeptide includes at least one modified sugar moiety such as arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

In yet another embodiment, the polypeptide is an α-anomeric polypeptide. An α-anomeric polypeptide forms specific double-stranded hybrids with complementary RNA in which, contrary to the usual β-units, the strands run parallel to each other (Gautier et al., *Nucl. Acids Res.* 15:6625-6641, 1987). The polypeptide may be conjugated to another molecule, for example a peptide, hybridization triggered cross-linking agent, transport agent, or hybridization-triggered cleavage agent. Polypeptide may include a targeting moiety that enhances uptake of the molecule by tumor cells. The targeting moiety may be a specific binding molecule, such as an antibody or fragment thereof that recognizes a molecule present on the surface of a B cell.

As an alternative to antisense inhibitors, catalytic nucleic acid compounds, such as ribozymes or anti-sense conjugates, may be used to inhibit gene expression. For example catalytic nucleic acids and anti-sense conjugates specific for the IL-21R or members of the Jak/Stat signaling pathway can be employed to modify an activity of a B cell. Ribozymes may be synthesized and administered to the subject, or may be encoded on an expression vector, from which the ribozyme is synthesized in the targeted cell (as in PCT publication WO 9523225, and Beigelman et al. *Nucl. Acids Res.* 23:4434-4442, 1995). Examples of oligonucleotides with catalytic activity are described in WO 9506764, WO 9011364, and Sarver et al., *Science* 247:1222-1225, 1990. Conjugates of antisense with a metal complex, e.g. terpyridylCu (II), capable of mediating mRNA hydrolysis, are described in Bashkin et al., *Appl. Biochem Biotechnol.* 54:43-56, 1995.

Particular antisense nucleic acids include a sequence complementary to at least a portion of an RNA transcript of an IL-21 or IL-21 receptor gene, such as a human IL-21 or IL-21 receptor gene. However, absolute complementarity, although advantageous, is not required. A sequence may be complementary to at least a portion of an RNA, meaning a sequence having sufficient complementarity to be able to hybridize with the RNA, forming a stable duplex; in the case of double-stranded IL-21 or IL-21 receptor antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an IL-21 or IL-21 receptor RNA it may contain and still form a stable duplex (or triplex, as the case may be). One skilled in the art can ascertain a tolerable degree of mismatch by use of standard procedures to determine the melting point of the hybridized complex.

The relative ability of polypeptide to bind to complementary strands is compared by determining the melting temperature of a hybridization complex of a polypeptide and its complementary strand. The melting temperature ($T_m$), a characteristic physical property of double helices, denotes the temperature in degrees Centigrade at which 50% helical versus coiled (unhybridized) forms are present. Base stacking, which occurs during hybridization, is accompanied by a reduction in UV absorption (hypochromicity). A reduction in WV absorption indicates a higher Tm. The higher the Tm the greater the strength of the binding of the hybridized strands. As close to optimal fidelity of base pairing as possible achieves optimal hybridization of an polypeptide to its target RNA.

Polynucleotides can be synthesized by standard methods known in the art, for example by use of an automated DNA synthesizer. Several different models of machines for synthesizing oligonucleotides are available (e.g. from Perkin-Elmer Applied Biosystems, 850 Lincoln Centre Drive, Foster City, Calif. 94404; Biosearch, Applied Biosystems, etc.). Furthermore, these machines can be programmed to allow the synthesis of oligonucleotides which contain the modified linkages mentioned above. After synthesis the oligonucleotides can be purified through capillary electrophoresis or other chromatography techniques. Phosphorothioate oligos may be synthesized by the method of Stein et al., *Nucl. Acids Res.* 16:3209, 1998, methylphosphonate oligos can be prepared by use of controlled pore glass polymer supports (Sarin et al., *Proc. Natl. Acad. Sci. USA* 85:7448-7451, 1988).

Another method of producing the antisense and catalytic nucleic acid molecules is the use of PCR. This particular method has the capability of generating longer polynucleotides than those normally produced through synthesis. This method involves tagging either the sense or antisense primer with an appropriate moiety, such as biotin. The moiety will then be used in subsequent purification. This allows the molecule that is complementary to the target sequence to be extracted from the complementary strand.

In a further embodiment, the agent that alters activity of a B cell is a soluble IL-21 receptor. The production of soluble receptors is well known in the art (see, for example, U.S. Pat. No. 6,403,087; U.S. Pat. No. 6,391,581). In one specific, non-limiting example, a soluble receptor is a receptor that lacks the sequences for insertion into the cell membrane. In another specific, non-limiting example, a soluble receptor is the IL-21 binding domain of the IL-21 receptor, fused a polypeptide that allows for secretion, such as an immunoglobulin polypeptide sequence (Fc). In another embodiment, the agent that alters activity of a B cell is a fragment of IL-21 that competes for binding of native IL-21 to the cell surface IL-21 receptor.

In yet a further embodiment, the agent that alters activity of a B cell is a chemical antagonist for the IL-21 receptor or an antagonist that otherwise inactivates the interaction of IL-21 with the IL-21 receptor, or that inactivates the cellular responsiveness to IL-21. Suitable antagonists include, but are not limited to, small molecules and other compounds that bind IL-21 or the IL-21 receptor but do not trigger the IL-21 signaling pathway. Similarly, an agent that alters the activity of a B cell can be a molecule that binds to and antagonizes molecules that are critical components of the IL-21 induced signaling pathway, such as Jak and Stat kinases.

Methods of Treatment

As demonstrated herein, the interaction of IL-21 with its receptor has an effect on immunoglobulin production. Thus, a method is provided for treating a subject with a disorder associated with IgE. In two examples the subject has Job's disorder or atopic disease. The method includes administering to the subject a therapeutically effective amount of IL-21 or an agonist thereof, thereby ameliorating a sign or a symptom of Job's disorder.

Job's syndrome is a disorder characterized by hyperimmunoglobulinemia E that is associated with eczema, recurrent respiratory infections, and "cold" staphylococcal skin abscesses of skin, lymph nodes and subcutaneous tissues. The laboratory findings in Job's syndrome are elevated IgE and defective chemotaxis. This syndrome affects fewer than 200,000 people in the United States. Job's syndrome (Hyper IgE syndrome) is typically inherited as an autosomal dominant trait, and has been mapped to a locus on the long arm of chromosome 4.

Atopic disease or immediate type hypersensitivity, such as atopic allergy, generally implies a familial tendency to manifest such conditions as asthma, rhinitis, urticaria, and eczematous dermatitis (atopic dermatitis) alone or in combination. However, individuals without an atopic background also may develop hypersensitivity reactions, particularly urticaria and anaphylaxis, associated with the same class of antibody, IgE, found in atopic individuals (Austin, In: Harrison's Principles of Internal Medicine 14th edition (Fauci et al., 1998, Ch. 310, p. 1860).

In one embodiment, a therapeutically effective amount of the IL-21 polypeptide is administered. In another embodiment, a nucleic acid sequences encoding an IL-21 molecule are is of use. One of skill in the art can readily produce and administer appropriate dosages of IL-21, or a nucleic acid encoding IL-21, to a subject. In a further embodiment, an agonist of IL-21 is administered, such as, but not limited to, a small molecule that binds to the IL-21 receptor and activates an intracellular signaling pathway.

As demonstrated herein, the interaction of IL-21 with its receptor is involved in modulating an activity of B cells. For example, the interaction of IL-21 with its receptor affects the production of immunoglobulins, such as IgG, IgE, and IgM. Thus, in one embodiment, an agent that interferes with the interaction of IL-21 and its receptor is of use in treating or preventing a number of disorders associated with increased production of an immunoglobulin. The method includes administering to a subject a therapeutically effective amount of an agent that interferes with the interaction of IL-21 with an IL-21 receptor, thereby altering a B cell activity in the subject.

In another embodiment, a method is provided for treating a subject who has, or is susceptible to, an allergic condition, such as asthma (for example, allergic asthma) or other respiratory problems. In a further embodiment, the subject has an inflammatory condition, including acute and chronic inflammatory conditions. Specific, non-limiting examples of inflammatory conditions are inflammation associated with infection (such as septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or a condition resulting from the over production of cytokines. In yet another embodiment, the subject has atopic dermatitis.

In a further embodiment, the subject has an autoimmune disorder. Specific, non-limiting examples of autoimmune disorders are Addison's disease, hemolytic anemia, antiphospholipid syndrome, rheumatoid arthritis, dermatitis, allergic encephalomyelitis, glomerulonephritis, Goodpastures Syndrome, Grave's Disease, Multiple Sclerosis, Myasthenia Gravis, Neuritis, Ophthalmia, Bullous Pemphigoid, Purpura, Autoimmune Thyroiditis, Systemic Lupus, Erythematosis, Autoimmune Pulmonary Inflammation, Guillain-Barre Syndrome, insulin dependent diabetes mellitis, and autoimmune inflammatory eye disease.

It should be noted that an agent that interferes with the interaction of IL-21 and its receptor can be administered to the subject with the allergic condition, inflammatory condition or autoimmune disorder alone or in combination with other peptides. In one embodiment, an agent that interferes with the interaction of IL-21 and its receptor is administered with an agent that interferes with the interaction of IL-4 and the IL-4 receptor. The agents are known to one of skill in the art (see, for example U.S. Pat. No. 6,358,509; U.S. Pat. No. 6,313,272, and U.S. Pat. No. 6,200,805). In another embodiment, the agent that inhibits the interaction of IL-21 with the IL-21 receptor is administered with another immunosuppressive agent, such as cyclosporine or FK506.

A composition including an agent that interferes with the interaction of IL-21 and its receptor with the can be prepared in accordance with standard techniques well known to those skilled in the pharmaceutical or veterinary arts. Such compositions can be administered in dosages and by techniques well known to those skilled in the medical or veterinary arts taking into consideration such factors as the age, sex, weight, species and condition of the particular patient, and the route of administration. An agent that interferes with the interaction of IL-21 and its receptor can be administered alone, or can be co-administered with other agents, or can be sequentially administered with "other" agent(s) or "other" immunological, antigenic or vaccine compositions thereby providing "cocktail" or combination compositions or administrations, and methods employing them.

If the agent is an antisense molecule or ribozyme that targets IL-21 or an IL-21 receptor mRNA, the amount of IL-21 or IL-21 receptor antisense nucleic acid which will be effective in the treatment of a particular disorder or condition will depend on the nature of the disorder or condition, and can be determined by standard clinical techniques. In a specific embodiment, pharmaceutical compositions comprising IL-21 or IL-21 receptor antisense nucleic acids are administered via liposomes, microparticles, or microcapsules. In various embodiments, it may be useful to use such compositions to achieve sustained release of the antisense nucleic acids. In a specific embodiment, it may be desirable to utilize liposomes targeted via antibodies to specific identifiable tumor antigens (Leonetti et al., *Proc. Natl. Acad. Sci. USA* 87:2448-2451, 1990; Renneisen et al., *J. Biol. Chem.* 265:16337-16342, 1990).

Alternatively, a vector which contains the DNA sequence encoding the therapeutic nucleic acid molecule can be used. Once the vector is delivered to the host cell, the cell will transcribe the DNA into the antisense or catalytic nucleic acid molecule. If the host cell is that of the patient this method accomplishes production and delivery of the molecule simultaneously.

The agent that interferes with the interaction of IL-21 and its receptor, or IL-21 itself, can be administered by any means known to one of skill in the art (see Banga, "Parenteral Controlled Delivery of Therapeutic Peptides and Proteins," in *Therapeutic Peptides and Proteins*, Technomic Publishing Co., Inc., Lancaster, Pa., 1995) such as by intramuscluar, subcutaneous, or intravenous injection, but even oral, nasal, or anal administration is contemplated. In one embodiment, administration is by subcutaneous or intramuscular injection. To extend the time during which the peptide or protein is available to stimulate a response, a peptide or protein can be provided as an implant, an oily injection, or as a particulate system. The particulate system can be a microparticle, a microcapsule, a microsphere, a nanocapsule, or similar particle. (see, e.g., Banga, supra). A particulate carrier based on a synthetic polymer has been shown to act as an adjuvant to enhance the immune response, in addition to providing a controlled release.

Thus, examples of compositions include liquid preparations for orifice (e.g., oral, nasal, anal, vaginal, peroral, intragastric) administration such as suspensions, syrups or elixirs; and, preparations for parenteral, subcutaneous, intradermal, intramuscular or intravenous administration (e.g., injectable administration, including the use of needleless injectors) such as sterile suspensions or emulsions, are provided. In such compositions the antigen(s) may be in admixture with a suitable carrier, diluent, or excipient such as sterile water, physiological saline, glucose or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard texts, such as Remington's Pharmaceutical Science, 17th edition, 1985, incorporated herein by reference, may be consulted to prepare suitable preparations, without undue experimentation. The compositions can also be lyophilized.

In one embodiment, the agent is a polypeptide, such as a soluble IL-21 receptor, that interferes with the interaction of IL-21 and the IL-21 receptor. Thus, nucleic acid sequences encoding an polypeptide, such as a soluble IL-21 receptor, that interferes with the interaction of IL-21 and its receptor are also of use. In addition, antisense nucleic acids and ribozymes that specifically inhibit the transcription of IL-21, or the IL-21 receptor, can also be administered to a subject.

Suitable dosages can also be based determined by one of skill in the art. Typical dosages of a polypeptide, such as, but not limited to, a soluble IL-21 receptor, can be from about 5 µg/ml to about 150 µg/ml, and other dosages can be from about 15 to about 150 µg/dose.

The compositions disclosed herein can be administered for therapeutic treatments. In therapeutic applications, compositions are administered to a subject having a disorder in a therapeutically effective amount, which is an amount sufficient to cure or at least partially arrest the disease or a sign or symptom of the disorder. Amounts effective for this use will depend upon the severity of the disorder and the general state of the patient's health. An effective amount of the compound is that which provides either subjective relief of a symptom(s) or an objectively identifiable improvement as noted by the clinician or other qualified observer.

Single or multiple administrations of the compositions are administered depending on the dosage and frequency as required and tolerated by the subject. In one embodiment, the dosage is administered once as a bolus, but in another embodiment can be applied periodically until either a therapeutic result is achieved. Generally, the dose is sufficient to treat or ameliorate symptoms or signs of disease without producing unacceptable toxicity to the subject.

As noted above, the dosage of the composition varies depending on the weight, age, sex, and method of administration. The dosage can also be adjusted by the individual physician as called for based on the particular circumstances. The compositions can be administered conventionally as vaccines containing the active composition as a predetermined quantity of active material calculated to produce the desired therapeutic or immunologic effect in association with the required pharmaceutically acceptable carrier or diluent (i.e., carrier or vehicle). For example, about 50 μg of a DNA construct vaccine can be injected intradermally three times at two week intervals to produce the desired therapeutic or immunologic effect. In another embodiment, an about 1 mg/Kg dosage of a protein vaccine can be injected intradermally three times at two week intervals to produce the desired therapeutic or immunologic effect.

The invention is illustrated by the following non-limiting Examples.

EXAMPLES

The IL-21 binding protein (IL-21 receptor, IL-21R) is a type I cytokine receptor that is most similar in sequence and expression pattern to the IL-2 receptor β chain (Ozaki et al., *Proc. Natl. Acad. Sci. USA* 97:11439, 2000; Parrish-Novak et al., *Nature* 408:57, 2000; see also Genbank Accession No. NP_851565 and Genbank Accession No. NP_068687, which are both incorporated herein by reference). IL-21 was initially reported to have a costimulatory effect on anti-CD3-induced T-cell proliferation, to augment NK-cell expansion and differentiation from human $CD34^+$ cells if cultured with IL-15 and Flt-3 ligand, and to augment B-cell proliferation in response to anti-CD40 but to inhibit B-cell proliferation to anti-IgM+IL-4 (Parrish-Novak et al., *Nature* 408:57, 2000). More recently, IL-21 was reported to not affect NK-cell development or expansion from murine splenocytes even when combined with IL-15, and in fact to oppose certain actions of IL-15 on activated NK cells (Kasaian et al., *Immunity* 16, 559, 2002). Like IL-2, IL-4, IL-7, IL-9, and IL-15 (Leonard, *Nature Rev. Immunol.* 1:200, 2001), the receptor for IL-21 contains the common cytokine receptor γ chain ($\gamma_c$) (Leonard, *Nature Rev. Immunol.* 1:200, 2001; Asao et al., *J. Immunol.* 167:1, 2001). Mutations in $\gamma_c$ result in X-linked severe combined immunodeficiency (XSCID) (Leonard, *Nature Rev. Immunol.* 1:200, 2001; Noguchi et al., *Cell* 73:147, 1993). In this disease, T and NK cells are absent; B-cell numbers are normal but the B cells are non-functional (Buckley et al., *J Pediatr.* 130:378, 1997). The absence of T and NK cells can be explained by defective signaling in response to IL-7 (von Freeden-Jeffry et al., *J. Exp. Med.* 181:1519, 1995; Peschon et al., *J. Exp. Med.* 180:1955, 1994; Puel et al., *Nat. Genet.* 20:394, 1998) and IL-15, respectively. However, no cytokine has so far been similarly linked to the lack of B-cell function in XSCID. As demonstrated herein, in addition to IL-4, IL-21 signaling also is essential for efficient IgG1 production and is vital for normal regulation of IgE production following immunization. Furthermore, it is demonstrated that IL-4 and IL-21 together are global regulators of antibody production.

Example 1

Generation of IL-$21R^{-/-}$ Mice

To generate IL-21 receptor knock-out (IL-$21R^{-/-}$) mice, a targeting construct was designed that eliminates the extracellular domain (see FIG. 1A). A bacterial artificial chromosome (BAC) clone library prepared from 129Sv mice (Genome Systems) was screened using a probe used to identify murine IL-21 receptor (IL-21R) cDNAs. A clone was identified that by restriction enzyme mapping contained all IL-21R coding exons. A targeting construct was then designed (FIG. 1A) to delete the coding region, extending from the signal peptide to the transmembrane domain, so that only 5 amino acids of the signal peptide were retained; the residual part of the cytoplasmic domain was frame-shifted. The targeting construct has 4-kb (Bam HI/Eco RI) and 2-kb (Xho I/Nhe I) 5' and 3' flanking fragments, respectively. The targeting construct, wild-type genomic locus and the homologously recombined locus are shown in FIG. 1A.

ES cells in which homologous recombination had occurred were injected into C57BL/6 blastocysts, and resulting chimeric mice were mated with C57BL/6 mice and heterozygous offspring were then interbred. Southern blot analyses of tail DNA using 5' (FIG. 1B) and 3' (FIG. 1C) probes confirmed homologous recombination, and RT-PCR of freshly isolated thyrnocytes confirmed the loss of IL-21R mRNA expression (FIG. 1D). The IL-21R gene is only ≈39 kb downstream of the IL-4RA gene on human chromosome 16 (Ozaki et al., *Proc. Natl. Acad. Sci. USA* 97:11439, 2000; Parrish-Novak et al., *Nature* 408:57, 2000) and correspondingly, analysis of the Celera murine database showed that the murine Il21r and Il4ra genes are closely positioned. It was hypothesized that disrupting the Il21r gene might affect IL-4Rα expression; however, both Th2 differentiated cells (FIG. 1E) and thymocytes (FIG. 1F) from IL-$21R^{-/-}$ mice had normal levels of IL-4Rα mRNA. In various T-cell and B-cell proliferation assays, IL-$21R^{-/-}$ mice could not respond to IL-21, suggesting that IL-21 can only exert its actions through a receptor containing IL-21R.

Example 2

Phenotype of IL-$21R^{-/-}$ Mice

Figure 2:
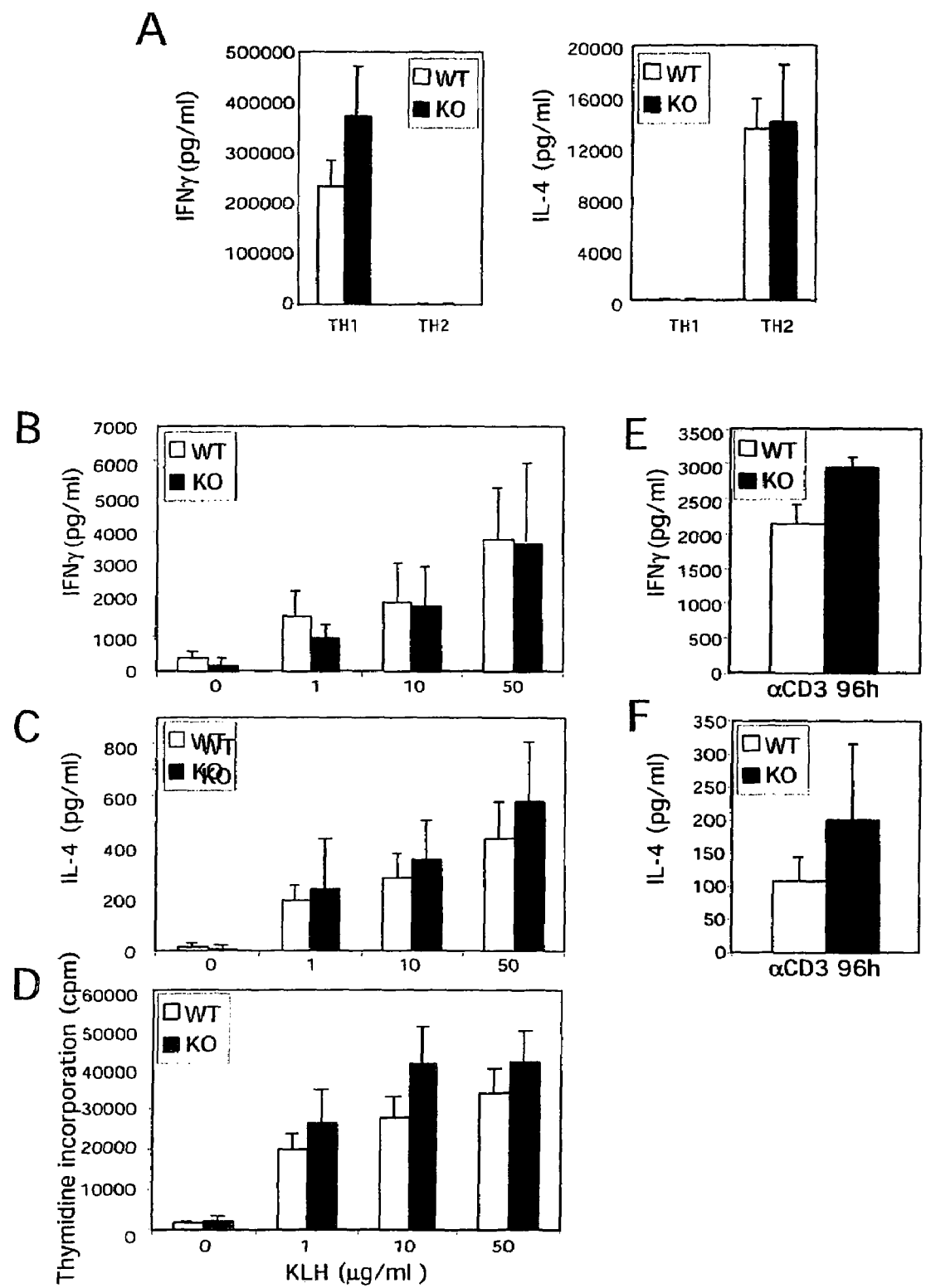
FIG. 2 is a set of bar graphs showing cytokine production from lymphocytes in vivo sensitized with KLH and in vitro cultured with either KLH or plate bound anti-CD3.

IL-$21R^{-/-}$ mice had a normal gross appearance and normal organ sizes. As IL-21R expression and the reported in vitro actions of IL-21 are primarily restricted to T, B, and NK cells (Ozaki et al., *Proc. Natl. Acad. Sci. USA* 97:11439, 2000; Parrish-Novak et al., *Nature* 408:57, 2000), the analysis of IL-$21R^{-/-}$ mice was focused on the immune system. By flow cytometric analyses, no significant differences were detected in thymocytes, splenocytes, peritoneal cells, and bone marrow cells using antibodies to CD3, CD4, CD5, CD8, CD21, CD23, CD25, CD43, CD44, CD62L, B220, IgM, IgD, DX5, Gr1, TER119, IL-2Rβ, $\gamma_c$, HSA, and BP-1. Moreover, freshly isolated IL-$21R^{-/-}$ splenocytes exhibited normal proliferation to plate-bound anti-CD3. When splenic $CD4^+$ T cells were stimulated with plate-bound anti-CD3 under Th1 or Th2 polarizing conditions, interferon gamma (IFNγ) and IL-4 production were not diminished in IL-$21R^{-/-}$ mice (FIG. 2A), suggesting that both Th1 and Th2 differentiation capacity was not impaired.

Proliferation assays were performed on purified B cells (>95% pure based on flow cytometry with B220).

Lipopolysaccharide (LPS), anti-CD40, and anti-IgM+IL-4 induced comparable proliferation in IL-21R$^{-/-}$ and wild type mice. Moreover, analysis of serum Ig levels from naïve animals revealed no obvious alteration in IgM, but IgG levels were approximately half that of wild type mice. IgG1 and IgG2b tended to be lower and IgE tended to be higher in IL-21R$^{-/-}$ mice, but these differences were not statistically significant.

To further investigate the role of IL-21, mice were immunized with keyhole limpet hemocyanin (KLH). After nine days, draining lymph nodes were excised and cultured in vitro with KLH for four days. Consistent with the normal in vitro Th cell differentiation, production of IFNγ (FIG. 2B) and IL-4 (FIG. 2C), as well as proliferation (FIG. 2D) were relatively similar in IL-21R$^{-/-}$ and wild type mice. Similarly, after four days stimulation in anti-CD3 coated plates, there was no defect in production of IFNγ (FIG. 2E) or IL-4 (FIG. 2F) in the IL-21R$^{-/-}$ mice.

Figure 3:
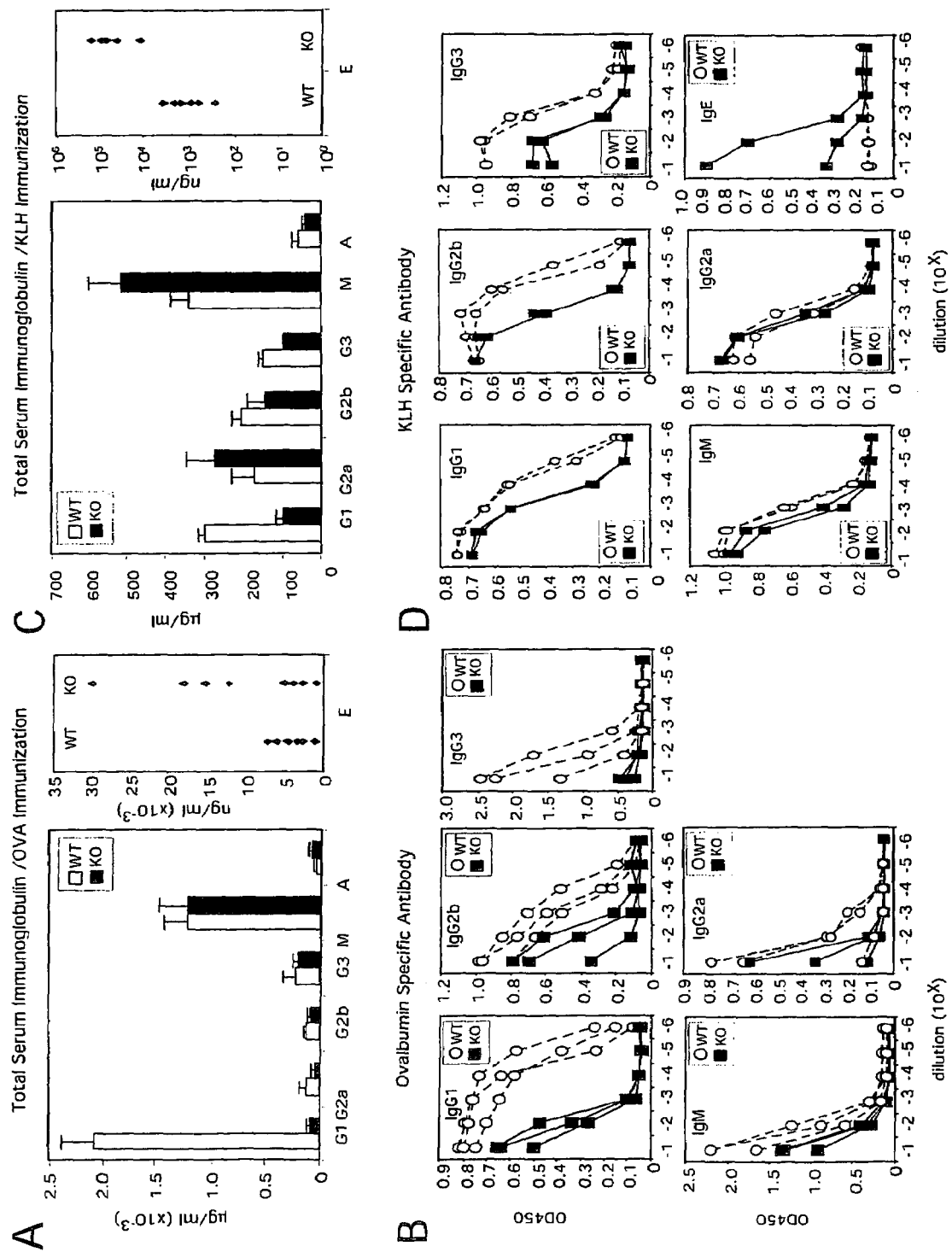
FIG. 3 is a set of graphs of results for total and antigen-specific Ig induced by immunization with ovalbumin (FIGS. 3A and 3B) or KLH (FIGS. 3C and 3D). Shown are the total Ig for each subclass (FIGS. 3A and 3C) and relative amount of antigen-specific Ig subclasses (FIGS. 3B and 3D) induced by immunization.

To evaluate B-cell function in vivo, mice were immunized with ovalbumin (OVA). Serum Ig levels were analyzed one week after a secondary immunization. The normal increase in IgG1 was markedly impaired in IL-2 R$^{-/-}$ mice, with total serum IgG1 20-25 fold lower (FIG. 3A, left) and antigen-specific IgG1 antibody approximately 1000 times lower than in wild type mice (FIG. 3B). There was no difference in total serum IgG2a, IgG2b, IgG3, IgM, and IgA (FIG. 3A, left), but ovalbumin-specific IgG2b and IgG3 were lower in IL-21R$^{-/-}$ mice (FIG. 3B), and total serum IgE levels in IL-21R$^{-/-}$ mice were variable but were markedly higher in some of the animals (FIG. 3A, right). When mice were immunized with keyhole limpet hemocyanin (KLH), the IgG1 response was again impaired, being approximately one third that seen with wild type mice (FIG. 3C, left). Like ovalbumin, KLH did not affect other total Ig levels except for a slight decrease in IgG3 (FIG. 3C, left); however, KLH-specific IgG1, IgG2b, and IgG3 were approximately 10-fold lower in IL-21R$^{-/-}$ mice (FIG. 3D). KLH-specific IgG1, IgG2b, and IgG3 were reduced about $\frac{1}{10}^{th}$ of the values for these subclasses in wildtype mice. Strikingly, IgE production in IL-21R$^{-/-}$ mice was markedly increased (≈50-55 fold) (FIG. 3C, right), as was KLH-specific IgE (FIG. 3D).

Figure 4:
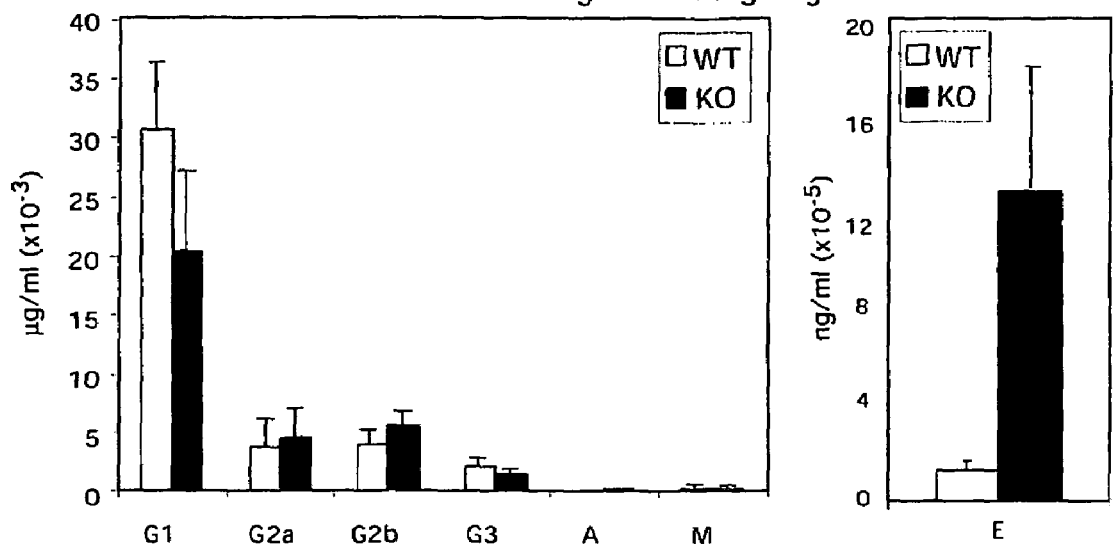
FIG. 4 is a set of graphs showing the total serum Ig levels after infection of anti-mouse IgD (FIG. 4A) and *Toxoplasma gondii* infection (FIG. 4B). For the data shown in FIG. 4A, three wild type and three IL-21R$^{-/-}$ mice were injected with 200 μl rat-anti-IgD subcutaneously, with 100 μl on each side of the abdomen, as previously described (Shimoda et al., Nature 380:630, 1996). After 8 days, serum Ig subclasses were measured as described above. For the data shown in FIG. 4B, *Toxoplasma gondii* (ME-49 strain) were intraperitoneally injected at a dose of 20 cysts per mouse and serum Ig was determined by ELISA at day 100 (6 survivors of 7 mice in each group were analyzed).
Figure 4:
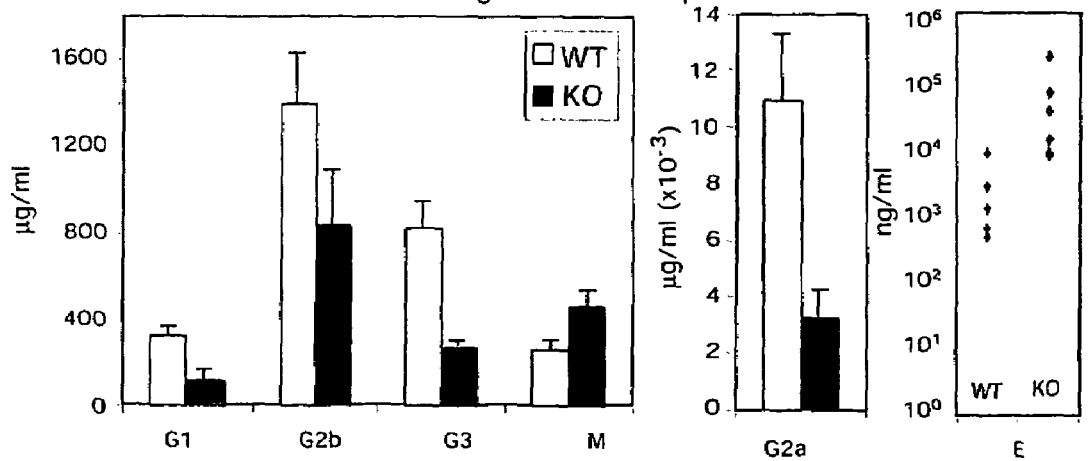

Mice were next injected with rat anti-mouse IgD, an inducer of IgG1 and IgE. Normal mice injected with IgD respond by day 8 with marked elevations of serum IgG1 and IgE. Eight days after injection of anti-IgD, serum IgE in IL-21R$^{-/-}$ mice was approximately 10 times higher than in wild type mice (FIG. 4A), whereas levels of Ig classes were more similar to those in wild type mice, with the tendency towards diminished IgG1 not achieving statistical significance in this system (FIG. 4A left).

Infection with *Toxoplasma gondii* induces strong Th1 differentiation and potent IFNγ production that is required for surviving the acute phase of the infection. IFNγ serum levels at day 5 were similar in wild type and IL-21R$^{-/-}$ mice. IFNγ levels following in vitro culture with *Toxoplasma* antigen were also comparable and 6 of 7 mice in both wild type and IL-21R groups survived for more than 100 days. Despite similar survival rates, at day 100, serum IgG1 was 3-fold lower (FIG. 4B, left) and IgE was approximately 20-25 higher (FIG. 4B, right) in the IL-21R$^{-/-}$ mice. This increase in IgE is particularly noteworthy given that there is not normally an IgE response in mice to *Toxoplasma gondii* (Suzuki et al., *J. Immunol.* 0.157:2564, 1996). IgG2b, IgG3, and IgG2a were also diminished as compared to wild type levels (FIG. 4B, left and center panels).

To determine whether the impaired IgG1 response and augmented IgE production resulted from an obvious intrinsic B-cell defect, purified B cells were cultured with anti-CD40+IL-4 or LPS+IL-4. IgG1 and IgE production was similar in IL-21R$^{-/-}$ and wild type B-cells (FIGS. 5A and 5B), suggesting that the Ig abnormality in IL-21R$^{-/-}$ mice is not related to an intrinsic B-cell defect.

Splenic CD4+T cells were stimulated with plate bound CD3-specific antibody under Th1 or Th2-polarizing conditions, but neither interferon (IFN)-γ nor IL-4 production was diminished. Thus, these differentiation pathways are not impaired. Moreover, when mice were immunized with KLH and spleen cells were restimulated in vitro, IFN-γ and IL-4, as well as proliferation, were relatively similar in IL-21R$^{-/-}$ mice and wild type controls. Spleen cells from IL-21R$^{-/-}$ mice and wild-type mice generated comparatively similar levels of IFN-γ and IL-4 after four days of stimulation on plates coated with 2C22 monoclonal antibody to CD3ε.

To determine whether the impaired IgG1 response and augmented IgE production resulted from on obvious B cell defect, purified B cells were co-cultured with either the combination of CD40 specific antibodies plus IL-4 or LPS plus IL-4. Prodcution of IgG1 and IgE was relatively similar in IL-21R$^{-/-}$ and wild-type B cells, consistent with the lack of a requirement of IL-21R for stimulation of B cells by these stimuli. However, the combination of CD40 specific antibodies plus IL-4 and IL-21 boosted IgG1 production in purified wild-type B cells to a significantly higher level than in the IL-21R$^{-/-}$ mice. Thus, Il-21 affects IgG1 production in normal murine B cells, and IL-21R$^{-/-}$ mice have an intrinsic B cell defect.

Figure 5:
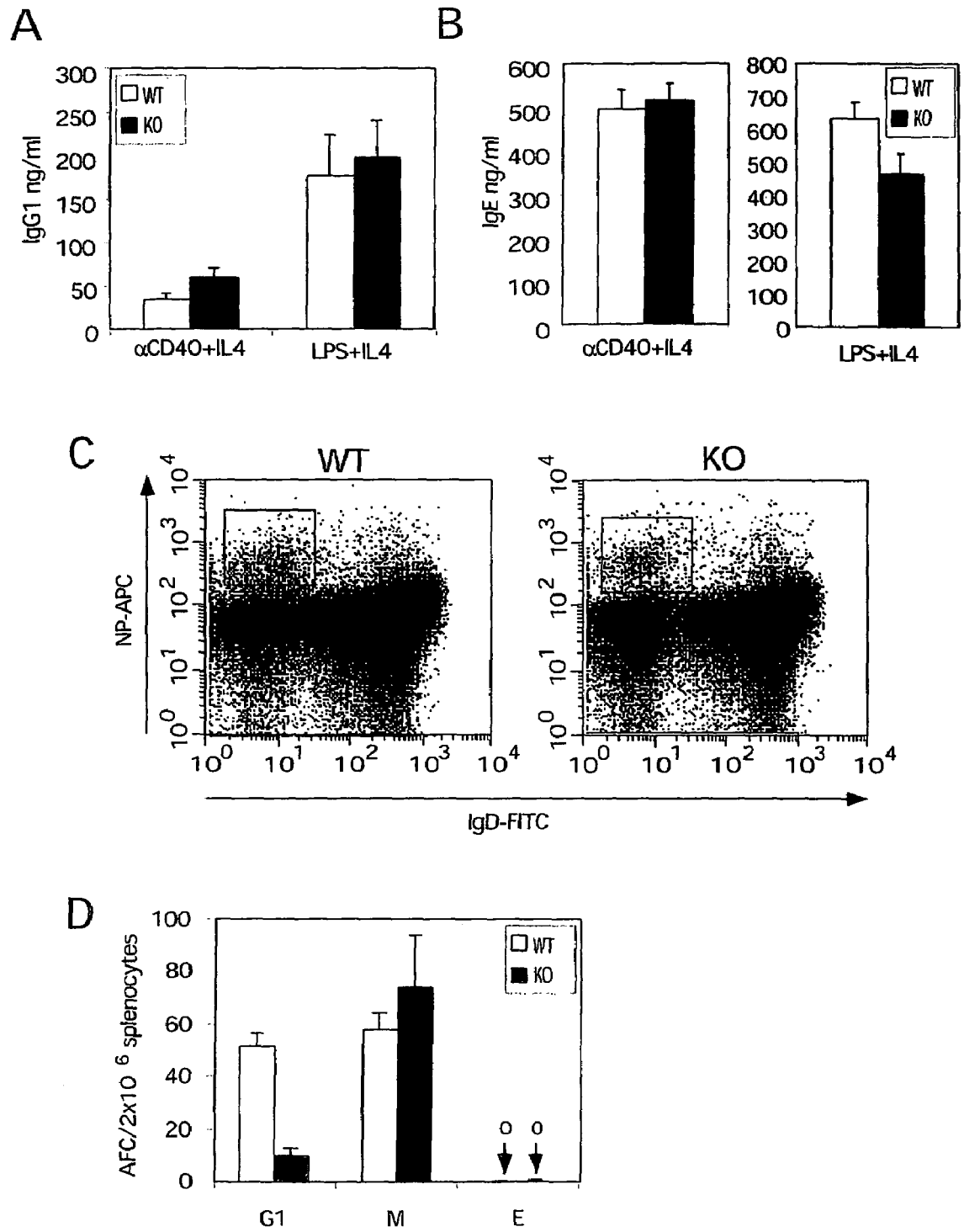
FIG. 5 is a set of images showing in vitro IgG1 and IgE production in IL-21R$^{-/-}$ mice.

To evaluate the ability of IL-21R$^{-/-}$ mice to develop antibody-forming cells and memory B-cells, mice were immunized with T-cell dependent antigen, nitrophenyl (NP)-conjugated KLH. After exposure to antigen, the number of antibody-forming cells were evaluated, such as hapten (NP)-specific antibody-secreting cells and memory B-cells as NP-specific antibody-expressing cells that did not express IgD, CD4, CD8, F4/80, and were propidium iodide-negative 17 (McHeyzer-Williams et al., *J. Exp. Med.* 191:1149, 2000; Driver et al., *L. J. Immunol.* 167:1393, 2001). In wild type and IL-21 R$^{-/-}$ mice, there was at most only a modest difference in the number of splenic memory cells based on IgD(−)/NP-Ig(+) staining patterns (FIG. 5C), but the number of hapten-specific IgG1-forming cells in the spleen was much lower in the IL-21R$^{-/-}$ mice (FIG. 5D). Thus, the decreased IgG1 could not be explained simply by a decrease in memory cells, but instead likely reflects diminished antigen-specific IgG1 producing cells. NP-specific IgG1 was also diminished.

Example 3

IL-4$^{-/-}$IL-21R$^{-/-}$ Double Knock-Out (KO) Mice

γ$_c$-deficient mice lack B-cell development (DiSanto et al., *Proc. Natl. Acad. Sci. USA* 92:377, 1995; Cao et al., *Immunity* 2:223, 1995) due to defective IL-7 signaling (DiSanto et al., *Proc. Natl. Acad. Sci. USA* 92:377, 1995; Cao et al., *Immunity* 2:223, 1995), whereas humans with XSCID have normal numbers of B-cells (Leonard, *Nature Rev. Immunol.* 1:200, 2001), presumably because of other or redundant signals besides IL-7 for B-cell development (Leonard, *Nature Rev. Immunol.* 1:200, 2001; Puel et al., *Nat. Genet.* 20:394, 1998). Nevertheless, humans with XSCID have markedly defective B-cell function (Small et al., *Hum. Immunol.* 25:181, 1989; Gougeon et al., *J. Immunol.* 145:

2873, 1990; Conley, *Clin. Immunol. Immunopathol.* 61:S94, 1991; Buckley et al., *FASEB J* 7:95A, 1993). Dogs with canine XSCID have a similar B-cell phenotype to humans with XSCID (Hartnett et al., *Vet. Immunol. Immunopathol.* 75:121, 2000). IL-21R$^{-/-}$ B-cells are functionally defective but not as defective as in human or canine XSCID.

It was hypothesized that if IL-7 signaling were left intact but if signaling by another $\gamma_c$-dependent cytokine, in addition to IL-21, were also inactivated, murine B-cells could be generated with a phenotype similar to that found in humans with XSCID. Thus, IL-4$^{-/-}$IL-21R$^{-/-}$ double KO mice were generated. The strong up-regulation of IgE levels seen in the IL-21R$^{-/-}$ mice completely disappeared in IL-4$^{-/-}$IL-21R$^{-/-}$ mice (FIG. 6A, lower right panel), indicating that the IgE up-regulation in IL-21R$^{-/-}$ mice was strictly dependent on IL-4. Naïve IL-4$^{-/-}$IL-21R$^{-/-}$ double KO mice exhibited low serum levels of IgA and IGG subclasses, most strikingly in IgG1. In contrast, serum IgM levels were relatively normal, which is analgous to observations made in humans with XSCID.

Figure 6:
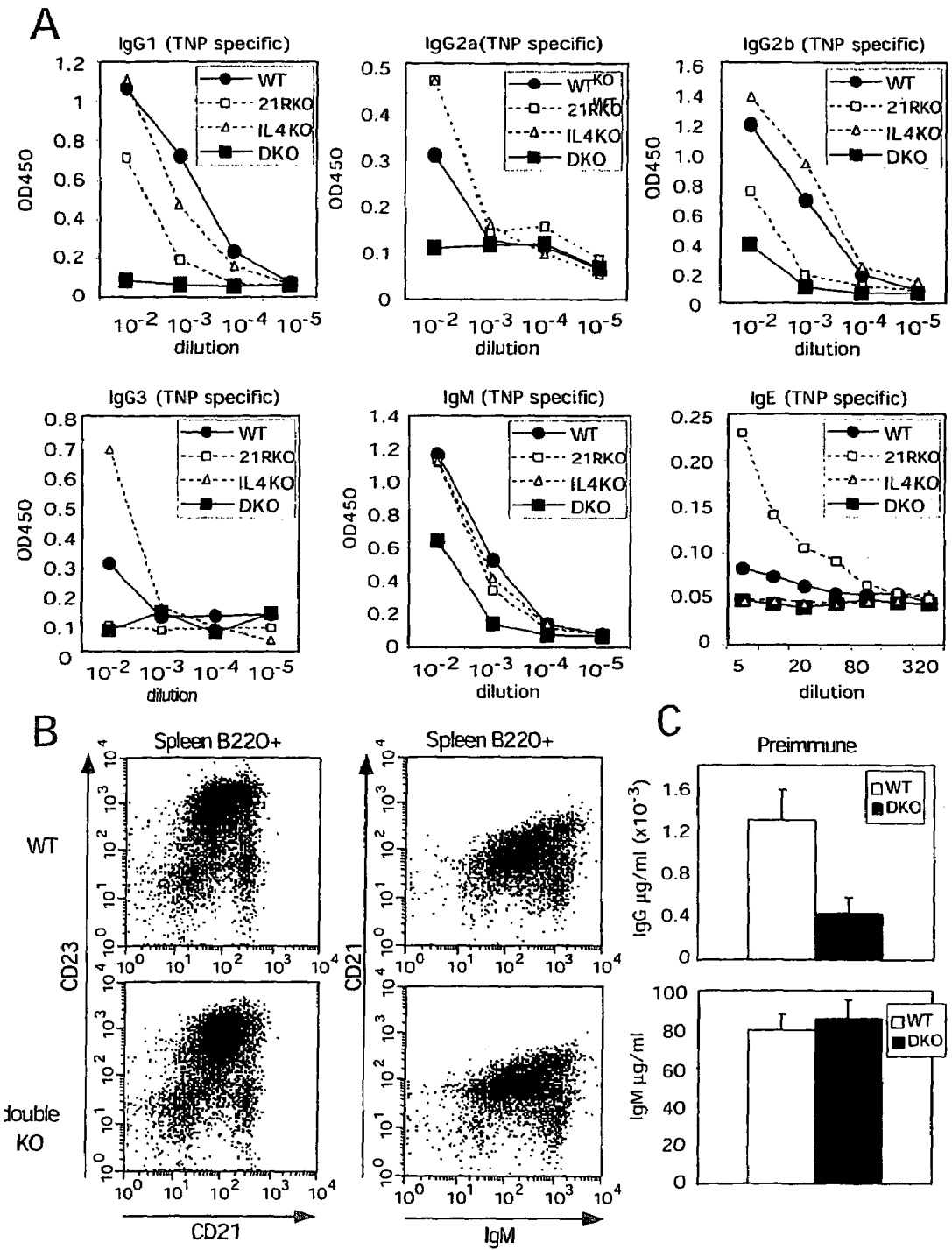
FIG. 6 is a set of images showing antigen-specific Ig production and flow cytometric analysis of splenic B cells in IL-4$^{-/-}$IL-21R$^{-/-}$ mice. For the results shown in FIG. 6A are graphs of results obtained using IL-4$^{-/-}$ mice in C57BL/6 background that were purchased from Jackson Laboratory. Serum TNP-specific Ig levels were measured by ELISA 10 days after a peritoneal injection of 2,4,6-trinitrophenyl (TNP)-chicken γ globulin (CGG) in CFA.

To further investigate Ig production by these animals, they were immunized with trinitrophenyl-conjugated chicken γ globulin (TNP-CGG), and the IL-4$^{-/-}$IL-21R$^{-/-}$ mice showed essentially no TNP-specific IgG1, IgG2a, IgG2b, IgG3, and only approximately 10% of normal levels of IgM production (FIG. 6A). Interestingly, B-cell numbers and B-cell maturation (based on CD23 vs. CD21 and IgM vs. CD21 staining) were comparable to that seen in wild type mice (FIG. 6B). Strikingly, the strong up-regulation of IgE seen in the IL-21R$^{-/-}$ mice completely disappeared in the IL-4$^{-/-}$IL-21R$^{-/-}$ double KO mice, which indicated that the increased IgE in IL-21R$^{-/-}$ mice was strictly dependent on IL-4.

The ability of the IL-4$^{-/-}$IL-21R$^{-/-}$ double KO mice to respond to two other antigens was evaluated. KLH induced a similar immunoglobulin profie to TNP-CGG, showing severely impaired production of KLH-specific IgG1, IgG2A, and IgG3, and only about 10-20% of normal levels of IgG2b and IgM production. The response to NP-KLH was also impaired, although the defects in IfG1, IgG2a, and IgG3 responses were less severe. Although germinal centers were relatively normal in mice lacking either IL-4 or IL-21R, in IL-4$^{-/-}$IL-21R$^{-/-}$ double KO mice germinal centers were disorganized, with decreased numbers of apoptotic bodies in marcrophages, consistent with diminished somatic mutation and defective affinity maturation. These results demonstrate a co-operative role for IL-4 and IL-21 for normal germinal center function.

However, IL-4$^{-/-}$IL-21R$^{-/-}$ mice exhibited pan-hypogammaglobulinemia in the naïve setting, with total IgG levels being approximately 33% of normal (FIG. 6C). In contrast to decreased levels of antigen-specific IgM (FIG. 6A), basal levels of total IgM were normal (FIG. 6C).

Thus, the IL-21/IL-21R system plays a vital role for B cell function in vivo. IL-21R$^{-/-}$ mice exhibited dysregulated IgG1 and IgE production. Following immunization the IL-4$^{-/-}$IL-21R$^{-/-}$ mice exhibited lower IgE, but unexpectedly, they clearly had a dramatic pan-hypogammaglobulinemia. Thus, as demonstrated herein, IL-21 is an important regulator of Ig production that functionally cooperates with IL-4. Although IL-4 plays an essential role in driving IgE class switch, the residual IgG1 production in IL-4 KO mice has suggested that there may be additional regulator(s) of IgG1 production. It is clearly shown in the experiments described herein that IL-21 is such a regulator. Moreover, IL-21R$^{-/-}$ mice provide a distinctive situation where IgE production is elevated but IgG1 is diminished.

As noted above, XSCID patients exhibit a major B cell defect. Even after successful reconstitution of T cells and NK cells following bone marrow transplantation, if donor B cells do not engraft, patients require chronic intravenous γ-globluin (Buckley et al., *N. Engl. J. Med.* 340:508, 1999). The results described herein indicate that the lack of IL-4 and IL-21 signaling largely explains the non-functional B-cells in XSCID. In humans, IL-7 signaling can be inactivated without loss of B-cell development, as demonstrated by the normal B-cell development in humans with XSCID, Jak3-deficient SCID, or IL-7Rα-deficient SCID. In contrast, the loss of IL-7 signaling in mice results in a loss of B-cell development, as is observed in mice lacking IL-7, IL-7Rα, Jak3, or $\gamma_c$. By generating mice defective in IL-4 and IL-21 signaling but which retain the action of IL-7 and thus have normal B-cell development, a phenotype has successfully be established in mice that closely resembles that found in B-cells of patients with XSCID. Thus, these mice can be used to screen agents of use in XSCID.

Example 4

IL-21 is Elevated in the BXSB-Yaa Autoimmune Mouse Model of Systemic Lupus Erythematosus The BXSB-Yaa mouse model is characterized by severe systemic lupus erythematosus (SLE), with lymphadenopathy, splenomegaly, leukocytosis, hypergammaglobulinemia, and severe immune-complex-mediated glomerulonephritis, often with a nephrotic syndrome. While the basis for the disease is unknown, severe SLE is dependent on the mutant Y chromosome-linked autoimmune accelerator Yaa locus. In contrast, mice carrying a C57BL/6 (B6)-derived wild-type Yaa allele exhibit a slowly developing chronic form of SLE.

Figure 7:
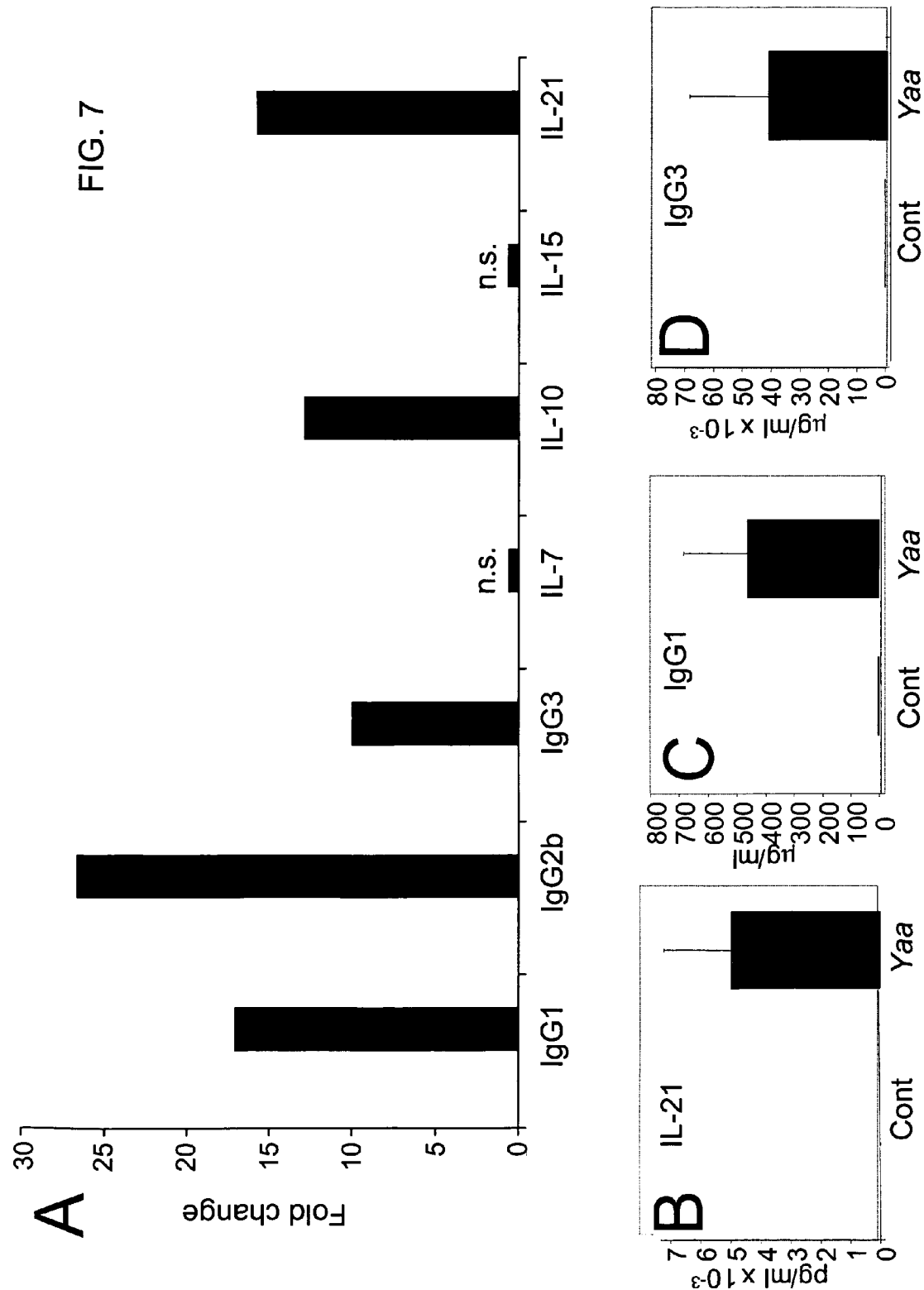
FIG. 7A-D is a series of bar graphs illustrating elevated IL-21 and IgG1 isotype expression in the BXSB-Yaa mouse. (A) Quantitative PCR (QPCR) analysis of 3 BXSB-Yaa compared with 3 BXSB-Yaa+16-week-old male mice. Of 231 expressed genes, nine genes were differentially expressed (at p<0.05) such that they exceeded the 0.400 GPR cutoff, and they had the following rank order: IgG2b (p<0.02), Il10 (p<0.02), IgG1 (p<0.03), Il21 (p<0.03), Dnase1 (p<0.04), IgG3 (p<0.04), Pdcd1 (p<0.05), Hsp70-1 (p<0.05), and Osteopontin (p<0.02), with IgG2b being the most highly induced. The fold expression changes for IgG2b, Il10, IgG1, Il21, and IgG3, as well as Il7 and Il15 are shown based on the normalizer gene, 18S RNA. Similar results including elevated Il21 expression, were obtain in two additional experiments. The genes for other cytokines that were examined, including Il1b, Il2, Il4, Il5, Il6, Il12p35, Il12p40, Il18, Il24, and Il25, did not manifest significant expression changes. mRNAs that are elevated in a small number of cells or that are present at relatively low abundance may not be detected in this assay, which further underscores the significance of the genes whose expression was induced. Although these animals clearly have plasma cells and hypergammaglobulinemia, the proportions of these cells in the whole spleen is presumably small, as classic markers of these cells, including XBP-1, CD-9, and Blimp-1 were not elevated. (B, C, and D) Markedly elevated levels of serum IL-21 (B), IgG1 (C), and IgG3 (D) in BXSB-Yaa mice, as determined by double antibody sandwich ELISA. Shown are means±SEM. The serum IL-21 levels in male BXSB-Yaa mice ranged between 62 and 13,900 pg/ml, whereas it was not detected in BXSB female mice. Serum IgG1 ranged between 16 and 2000 µg/ml for BXSB-Yaa males, whereas the BXSB female controls had approximately 3.2 µg/ml; serum IgG3 ranged between 80 and a remarkable 50,000 µg/ml for BXSB-Yaa males, whereas the BXSB female controls had approximately 30 µg/ml.

Examination of splenocytes for expression of multiple genes revealed a striking age-dependent increase in IL-21 mRNA levels in BXSB-Yaa mice, compared with BXSB-Yaa+WT male mice (FIG. 7A). Interestingly, the expression of the genes encoding IL-7 and IL-15, two other γc-dependent cytokines, did not differ significantly in BXSB-Yaa and BXSB-Yaa+WT mice (FIG. 7A). Like IL-21, IL-10 mRNA levels were also elevated in the BXSB-Yaa mouse (FIG. 7A). Corresponding to the increase in IL-21 mRNA, IgG1, IgG2b, and IgG3 mRNA levels were significantly elevated in BXSB-Yaa mice (FIG. 7A), as were serum levels of IL-21, IgG1, and IgG3 (FIGS. 7B, 7C, and 7D). Thus, in addition to elevated Ig levels, among cytokines examined, IL-21 was substantially increased in this model of SLE, suggesting that elevated levels of this cytokine are involved in the pathogenesis of this disease. This is consistent with the fact that the SLE-like autoimmune disease in these animals is dependent on CD4+ T cells, the major source of IL-21. Increased expression of IL-21 mRNA has also been detected in autoimmune NOD mice. Thus, IL-21 is critically involved in the pathogenesis of autoimmune disease.

Antagonists of IL-21 receptor binding and/or signaling can be used to treat subjects with autoimmune disorders such as SLE. Any of the agents disclosed herein that inhibit binding of IL-21 to the IL-21 receptor, and/or that inhibit IL-21 induced intracellular signaling can be used to treat a subject with an autoimmune disease. For example, an IL-21/IL-21R antagonist that inhibits signaling induced by IL-21 can be administered to subjects with an autoimmune disease, such as SLE to ameliorate symptoms of the disease. Alternatively, soluble receptors, fusion proteins or antibodies that block binding of IL-21 to the IL-21R can be employed. Similarly, peptides and small molecules that interfere with IL-21 binding or signaling can be used to treat an autoimmune disease. When treating a human subject, it can be desirable to administer a human or humanized peptide or polypeptide antagonist. For example, an antagonist that corresponds partially or completely in sequence to the human IL-21 receptor, or that incorporates additional human components can be administered to reduce the likelihood of an adverse immune response to the therapeutic antagonist. For example, a soluble human receptor, e.g., a soluble human IL-21R receptor can be administered to a human subject as an antagonist to treat SLE and other autoimmune disorders. Similarly, when the antagonist incorporates additional polypeptide components it can be preferable to administer antagonists incorporating additional human or humanized polypeptides, such as a human immunoglobulin Fc region polypeptide, or a modified polypeptide that is treated immunologically as human by the subject's immune system.

A variety of autoimmune diseases can be treated by administering an IL-21/IL-21R antagonist. For example, rheumatoid arthritis, myasthenia gravis, insulin-dependent diabetes mellitus, Hashimoto's thyroiditis, Graves disease, idiopathic thrombocytopenia purpura, hypertrophic cardiomyopathy, pernicious anemia, Goodpasture's syndrome, IgA nephropathy, autoimmune hepatitis, chronic active hepatitis, primary biliary cirrhosis, pemphigus, vitiligo, dermatitis herpetiformis, vitiligo, autoimmune astritis, autoimmune bowel disease, Addison's disease, Sjogren's syndrome, uveitis, or multiple sclerosis can be treated by administering an IL-21/IL-21R antagonist.

It will be apparent that the precise details of the methods or compositions described may be varied or modified without departing from the spirit of the described invention. We claim all such modifications and variations that fall within the scope and spirit of the claims below.

We claim:

1. A transgenic mouse whose somatic and germ cells comprise a disrupted endogenous IL-21 receptor gene, the disruption being sufficient to inhibit the binding of IL-21 to an IL-21 receptor, and a disrupted endogenous IL-4 gene, the disruption being sufficient to inhibit the production of IL-4 or the binding of IL-4 to the IL-4 receptor, the disruption being introduced into the mouse or an ancestor of the mouse at an embryonic stage, wherein the transgenic mouse has a genome homozygous for the disruption in an endogenous IL-21 receptor gene and homozygous for the disruption in an endogenous IL-4 gene, and wherein the mouse has diminished B cell function.

2. The transgenic mouse of claim 1, wherein the mouse has pan-hypogammaglobulinemia.

3. The transgenic mouse of claim 1, wherein the mouse is deficient in the production of an immunoglobulin.

4. The transgenic mouse of claim 3, wherein the immunoglobulin is an IgG1, IgG2a, IgG2b, or IgG3.

5. The transgenic mouse of claim 3, wherein the immunoglobulin is IgE.

* * * * *

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial sequence
<220> FEATURE:
<223> OTHER INFORMATION: primer

<400> SEQUENCE: 1
atgccccggg gcccagtggc tg                                      22

<210> SEQ ID NO 2
<211> LENGTH: 25
<212> TYPE: DNA
<213> ORGANISM: Artificial sequence
<220> FEATURE:
<223> OTHER INFORMATION: primer

<400> SEQUENCE: 2
cacagcatag gggtctctga ggttc                                   25

<210> SEQ ID NO 3
<211> LENGTH: 23
<212> TYPE: DNA
<213> ORGANISM: Artificial sequence
<220> FEATURE:
<223> OTHER INFORMATION: primer

<400> SEQUENCE: 3
atggtgaagg tcggtgtgaa cgg                                     23

<210> SEQ ID NO 4
<211> LENGTH: 24
<212> TYPE: DNA
<213> ORGANISM: Artificial sequence
<220> FEATURE:
<223> OTHER INFORMATION: primer

<400> SEQUENCE: 4
cccttccaca atgccaaagt tgtc                                    24

<210> SEQ ID NO 5
<211> LENGTH: 21
<212> TYPE: DNA
<213> ORGANISM: Artificial sequence
```

```
<220> FEATURE:
<223> OTHER INFORMATION: primer

<400> SEQUENCE: 5
atggggcggc tttgcaccaa g                                            21

<210> SEQ ID NO 6
<211> LENGTH: 21
<212> TYPE: DNA
<213> ORGANISM: Artificial sequence
<220> FEATURE:
<223> OTHER INFORMATION: primer

<400> SEQUENCE: 6
taggactcca ctcactccag g                                            21
```